(12) United States Patent
Penner et al.

(10) Patent No.: US 12,396,755 B2
(45) Date of Patent: Aug. 26, 2025

(54) METHODS AND APPARATUS FOR JOINT REPAIR

(71) Applicant: WRIGHT MEDICAL TECHNOLOGY, INC., Memphis, TN (US)

(72) Inventors: Murray John Penner, Vancouver (CA); Shawn E. McGinley, Arlington, TN (US); Jesse G. Moore, Germantown, TN (US); William Bragg, Lakeland, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 359 days.

(21) Appl. No.: 18/062,071

(22) Filed: Dec. 6, 2022

(65) Prior Publication Data

US 2023/0240718 A1    Aug. 3, 2023

Related U.S. Application Data

(60) Provisional application No. 63/267,240, filed on Jan. 28, 2022.

(51) Int. Cl.
*A61B 17/56* (2006.01)
*A61B 17/16* (2006.01)
(Continued)

(52) U.S. Cl.
CPC ........ *A61B 17/562* (2013.01); *A61B 17/1633* (2013.01); *A61B 17/1642* (2013.01);
(Continued)

(58) Field of Classification Search
CPC .............. A61B 17/562; A61B 17/1633; A61B 17/1642; A61B 17/1682; A61B 17/1775;
(Continued)

(56) References Cited

U.S. PATENT DOCUMENTS 3,839,742 A    10/1974 Link
3,872,519 A    3/1975  Giannestras et al.
(Continued)

FOREIGN PATENT DOCUMENTS

CA    2836651       3/2016
CN    101790353     7/2010
(Continued)

OTHER PUBLICATIONS

Extended European Search Report issued in connection with corresponding European Patent Application No. 22215287.8, Jun. 14, 2023, 10 pages.
(Continued)

*Primary Examiner* — Marcela I. Shirsat
(74) *Attorney, Agent, or Firm* — DUANE MORRIS LLP

(57) ABSTRACT

The disclosed subject matter relates to a system and method for preparing a surface of a bone proximate a joint, in which the preparation includes boring a plurality of arced channels/troughs in the bone surface using an arch drill assembly guided by plural guide bores along a predetermined longitudinal arc. The bored troughs create a scalloped surface on the bone to which an inverse contoured joint insert/implant having cooperating convex ridges engages. The plural guide bores are also defined by the predetermined longitudinal arc which may be circular or helical. The disclosed subject matter minimizes bone removal and allows greater access options for preparing the bone surface.

17 Claims, 21 Drawing Sheets

(51) Int. Cl.
| | |
|---|---|
| *A61B 17/17* | (2006.01) |
| *A61B 17/72* | (2006.01) |
| *A61F 2/30* | (2006.01) |
| *A61F 2/42* | (2006.01) |
| *A61F 2/46* | (2006.01) |
| *A61F 2/66* | (2006.01) |

(52) U.S. Cl.
CPC ...... *A61B 17/1682* (2013.01); *A61B 17/1775* (2016.11); *A61B 17/1739* (2013.01); *A61B 2017/564* (2013.01); *A61B 2017/567* (2013.01); *A61B 2017/568* (2013.01); *A61B 17/7291* (2013.01); *A61F 2002/30878* (2013.01); *A61F 2002/30879* (2013.01); *A61F 2002/30891* (2013.01); *A61F 2002/30892* (2013.01); *A61F 2/4202* (2013.01); *A61F 2002/4205* (2013.01); *A61F 2002/4207* (2013.01); *A61F 2/4606* (2013.01); *A61F 2/6607* (2013.01)

(58) Field of Classification Search
CPC . A61B 17/1631; A61B 17/1662; A61B 17/17; A61B 17/1739; A61B 17/7291; A61B 2017/564; A61B 2017/568; A61B 2017/567; A61F 2/4202; A61F 2/4606; A61F 2/6607; A61F 2/42; A61F 2002/30878; A61F 2002/30879; A61F 2002/30891; A61F 2002/30892; A61F 2002/30894; A61F 2002/4205; A61F 2002/4207
USPC ........... 606/80, 902, 915, 86 B, 104, 96, 98, 606/86 R, 87, 280
See application file for complete search history.

(56) References Cited

U.S. PATENT DOCUMENTS

| | | |
|---|---|---|
| 3,886,599 A | 6/1975 | Schlein |
| 3,889,300 A | 6/1975 | Smith |
| 3,896,502 A | 7/1975 | Lennox |
| 3,896,503 A | 7/1975 | Freeman et al. |
| 3,975,778 A | 8/1976 | Newton, III |
| 3,987,500 A | 10/1976 | Schlein |
| 4,021,864 A | 5/1977 | Waugh |
| 4,069,518 A | 1/1978 | Groth, Jr. et al. |
| 4,156,944 A | 6/1979 | Schreiber et al. |
| 4,166,292 A | 9/1979 | Bokros |
| 4,204,284 A | 5/1980 | Koeneman |
| 4,232,404 A | 11/1980 | Samuelson et al. |
| 4,309,778 A | 1/1982 | Buechel et al. |
| 4,470,158 A | 9/1984 | Pappas et al. |
| 4,755,185 A | 7/1988 | Tarr |
| 4,968,316 A | 11/1990 | Hergenroeder |
| 5,041,139 A | 8/1991 | Brånemark |
| 5,312,412 A | 5/1994 | Whipple |
| 5,326,365 A | 7/1994 | Alvine |
| 5,354,300 A | 10/1994 | Goble et al. |
| 5,395,188 A | 3/1995 | Bailey et al. |
| 5,423,825 A | 6/1995 | Levine |
| 5,476,466 A | 12/1995 | Barrette et al. |
| 5,601,563 A | 2/1997 | Burke et al. |
| 5,628,749 A | 5/1997 | Vendrely et al. |
| 5,634,927 A | 6/1997 | Houston et al. |
| 5,667,511 A | 9/1997 | Vendrely et al. |
| 5,674,223 A | 10/1997 | Cipolletti et al. |
| 5,735,904 A | 4/1998 | Pappas |
| 5,766,259 A | 6/1998 | Sammarco |
| 5,776,200 A | 7/1998 | Johnson et al. |
| 5,817,097 A | 10/1998 | Howard et al. |
| 5,824,106 A | 10/1998 | Fournal |
| 5,879,389 A | 3/1999 | Koshino |
| 5,885,299 A | 3/1999 | Winslow et al. |
| 5,888,203 A | 3/1999 | Goldberg |
| 5,897,559 A | 4/1999 | Masini |
| 5,935,132 A | 8/1999 | Bettuchi et al. |
| 6,002,859 A | 12/1999 | DiGioia, III et al. |
| 6,033,405 A | 3/2000 | Winslow et al. |
| 6,053,922 A | 4/2000 | Krause et al. |
| 6,102,952 A | 8/2000 | Koshino |
| 6,183,519 B1 | 2/2001 | Bonnin et al. |
| 6,245,109 B1 | 6/2001 | Mendes et al. |
| 6,342,056 B1 | 1/2002 | Mac-Thiong et al. |
| 6,344,043 B1 | 2/2002 | Pappas |
| 6,409,767 B1 | 6/2002 | Pericé et al. |
| 6,436,146 B1 | 8/2002 | Hassler et al. |
| 6,478,800 B1 | 11/2002 | Fraser et al. |
| 6,520,964 B2 | 2/2003 | Tallarida et al. |
| 6,530,930 B1 | 3/2003 | Marino et al. |
| 6,602,259 B1 | 8/2003 | Masini |
| 6,610,067 B2 | 8/2003 | Tallarida et al. |
| 6,610,095 B1 | 8/2003 | Pope et al. |
| 6,620,168 B1 | 9/2003 | Lombardo et al. |
| 6,645,215 B1 | 11/2003 | McGovern et al. |
| 6,663,669 B1 | 12/2003 | Reiley |
| 6,673,116 B2 | 1/2004 | Reiley |
| 6,679,917 B2 | 1/2004 | Ek |
| 6,719,799 B1 | 4/2004 | Kropf |
| 6,824,567 B2 | 11/2004 | Tornier et al. |
| 6,852,130 B2 | 2/2005 | Keller et al. |
| 6,860,902 B2 | 3/2005 | Reiley |
| 6,863,691 B2 | 3/2005 | Short et al. |
| 6,875,222 B2 | 4/2005 | Long et al. |
| 6,875,236 B2 | 4/2005 | Reiley |
| 6,926,739 B1 | 8/2005 | O'Connor et al. |
| 6,939,380 B2 | 9/2005 | Guzman |
| 6,942,670 B2 | 9/2005 | Heldreth et al. |
| 6,964,663 B2 | 11/2005 | Grant et al. |
| 7,001,394 B2 | 2/2006 | Gundlapalli et al. |
| 7,011,687 B2 | 3/2006 | Deffenbaugh et al. |
| 7,025,790 B2 | 4/2006 | Parks et al. |
| 7,163,541 B2 | 1/2007 | Ek |
| 7,238,190 B2 | 7/2007 | Schon et al. |
| 7,252,684 B2 | 8/2007 | Dearnaley |
| 7,314,488 B2 | 1/2008 | Reiley |
| 7,323,012 B1 | 1/2008 | Stone et al. |
| 7,476,227 B2 | 1/2009 | Tornier et al. |
| 7,481,814 B1 | 1/2009 | Metzger |
| 7,485,147 B2 | 2/2009 | Papps et al. |
| 7,534,246 B2 | 5/2009 | Reiley et al. |
| 7,534,270 B2 | 5/2009 | Ball |
| 7,615,082 B2 | 11/2009 | Naegerl et al. |
| 7,618,421 B2 | 11/2009 | Axelson, Jr. et al. |
| 7,625,409 B2 | 12/2009 | Saltzman et al. |
| 7,641,697 B2 | 1/2010 | Reiley |
| 7,678,151 B2 | 3/2010 | Ek |
| 7,713,305 B2 | 5/2010 | Ek |
| 7,717,920 B2 | 5/2010 | Reiley |
| 7,763,080 B2 | 7/2010 | Southworth |
| 7,803,158 B2 | 9/2010 | Hayden |
| 7,850,698 B2 | 12/2010 | Straszheim-Morley et al. |
| 7,896,883 B2 | 3/2011 | Ek et al. |
| 7,896,885 B2 | 3/2011 | Miniaci et al. |
| 7,909,882 B2 | 3/2011 | Stinnette |
| 7,914,533 B2 | 3/2011 | Nelson et al. |
| 7,963,996 B2 | 6/2011 | Saltzman et al. |
| 8,002,841 B2 | 8/2011 | Hasselman |
| 8,012,217 B2 | 9/2011 | Strzepa et al. |
| 8,034,114 B2 | 10/2011 | Reiley |
| 8,034,115 B2 | 10/2011 | Reiley |
| 8,048,164 B2 | 11/2011 | Reiley |
| 8,110,006 B2 | 2/2012 | Reiley |
| 8,114,091 B2 | 2/2012 | Ratron et al. |
| 8,128,627 B2 | 3/2012 | Justin et al. |
| 8,167,888 B2 | 5/2012 | Steffensmeier |
| 8,172,850 B2 | 5/2012 | McMinn |
| 8,177,841 B2 | 5/2012 | Ek |
| 8,192,434 B2 | 6/2012 | Huebner et al. |
| 8,268,007 B2 | 9/2012 | Barsoum et al. |
| 8,303,667 B2 | 11/2012 | Younger |
| 8,313,492 B2 | 11/2012 | Wong et al. |
| 8,317,797 B2 | 11/2012 | Rasmussen |

(56) References Cited

U.S. PATENT DOCUMENTS

| | | |
|---|---|---|
| 8,323,346 B2 | 12/2012 | Tepic |
| 8,337,503 B2 | 12/2012 | Lian |
| 8,361,159 B2 | 1/2013 | Ek |
| 8,366,559 B2 | 2/2013 | Papenfuss et al. |
| 8,430,879 B2 | 4/2013 | Stoneburner et al. |
| 8,475,463 B2 | 7/2013 | Lian |
| 8,491,596 B2 | 7/2013 | Long et al. |
| 8,579,980 B2 | 11/2013 | DeLurio et al. |
| 8,715,362 B2 | 5/2014 | Reiley et al. |
| 8,808,303 B2 | 8/2014 | Stemniski et al. |
| 8,911,444 B2 | 12/2014 | Bailey |
| 9,259,250 B2 | 2/2016 | Saravia et al. |
| 9,480,571 B2 | 11/2016 | McGinley et al. |
| 9,492,281 B2 | 11/2016 | Rouyer et al. |
| 9,629,726 B2 | 4/2017 | Reiley et al. |
| 9,629,730 B2 | 4/2017 | Reiley |
| 9,907,561 B2 | 3/2018 | Luna et al. |
| 10,034,678 B2 | 7/2018 | Park et al. |
| 10,039,558 B2 | 8/2018 | Park et al. |
| 10,111,674 B2 | 10/2018 | Crainich et al. |
| 10,136,904 B2 | 11/2018 | McGinley et al. |
| 10,149,687 B2 | 12/2018 | McGinley et al. |
| 10,182,832 B1 | 1/2019 | Saltzman et al. |
| 10,206,688 B2 | 2/2019 | Park et al. |
| 10,743,999 B2 | 8/2020 | Reiley |
| 10,940,012 B2 | 3/2021 | Sander et al. |
| 11,013,520 B2 | 5/2021 | Gareiss et al. |
| 2002/0068977 A1 | 6/2002 | Jackson |
| 2002/0082607 A1 | 6/2002 | Heldreth et al. |
| 2002/0133164 A1 | 9/2002 | Williamson |
| 2002/0173853 A1 | 11/2002 | Corl, III et al. |
| 2003/0208280 A1 | 11/2003 | Tohidi |
| 2003/0236522 A1 | 12/2003 | Long et al. |
| 2004/0030399 A1 | 2/2004 | Asencio |
| 2004/0039394 A1 | 2/2004 | Conti et al. |
| 2004/0068322 A1 | 4/2004 | Ferree |
| 2004/0167631 A1 | 8/2004 | Luchesi et al. |
| 2004/0186585 A1 | 9/2004 | Feiwell |
| 2004/0193268 A1 | 9/2004 | Hazebrouck |
| 2004/0216259 A1 | 11/2004 | Ponziani |
| 2004/0236431 A1 | 11/2004 | Sekel |
| 2005/0004676 A1 | 1/2005 | Schon et al. |
| 2005/0165408 A1 | 7/2005 | Puno et al. |
| 2005/0192674 A1 | 9/2005 | Ferree |
| 2005/0267481 A1 | 12/2005 | Carl et al. |
| 2006/0009857 A1 | 1/2006 | Gibbs et al. |
| 2006/0020345 A1 | 1/2006 | O'Connor et al. |
| 2006/0036257 A1 | 2/2006 | Steffensmeier |
| 2006/0116679 A1 | 6/2006 | Lutz et al. |
| 2006/0142870 A1 | 6/2006 | Robinson et al. |
| 2006/0229730 A1 | 10/2006 | Reiley et al. |
| 2006/0235541 A1 | 10/2006 | Hodorek |
| 2006/0247788 A1 | 11/2006 | Ross |
| 2007/0038303 A1 | 2/2007 | Myerson et al. |
| 2007/0100346 A1 | 5/2007 | Wyss et al. |
| 2007/0112431 A1 | 5/2007 | Kofoed |
| 2007/0162025 A1 | 7/2007 | Tornier et al. |
| 2007/0173944 A1 | 7/2007 | Keller et al. |
| 2007/0173947 A1 | 7/2007 | Ratron |
| 2007/0213830 A1 | 9/2007 | Ammann et al. |
| 2007/0233129 A1 | 10/2007 | Bertagnoli et al. |
| 2007/0276400 A1 | 11/2007 | Moore et al. |
| 2007/0288030 A1 | 12/2007 | Metzger et al. |
| 2008/0015602 A1 | 1/2008 | Axelson |
| 2008/0097617 A1 | 4/2008 | Fellinger et al. |
| 2008/0103603 A1 | 5/2008 | Hintermann |
| 2008/0109081 A1 | 5/2008 | Bao et al. |
| 2008/0195233 A1 | 8/2008 | Ferrari et al. |
| 2008/0215156 A1 | 9/2008 | Duggal et al. |
| 2008/0287954 A1 | 11/2008 | Kunz et al. |
| 2008/0306605 A1* | 12/2008 | Hasselman ........ A61B 17/1775 |
| | | 623/21.18 |
| 2008/0312745 A1 | 12/2008 | Keller et al. |
| 2009/0024131 A1 | 1/2009 | Metzger et al. |
| 2009/0043309 A1 | 2/2009 | Rasmussen |
| 2009/0043310 A1 | 2/2009 | Rasmussen |
| 2009/0054992 A1 | 2/2009 | Landes et al. |
| 2009/0082875 A1 | 3/2009 | Long |
| 2009/0105767 A1 | 4/2009 | Reiley |
| 2009/0105840 A1 | 4/2009 | Reiley |
| 2009/0182433 A1 | 7/2009 | Reiley et al. |
| 2009/0198341 A1 | 8/2009 | Choi et al. |
| 2009/0234360 A1 | 9/2009 | Alexander |
| 2009/0276052 A1 | 11/2009 | Regala et al. |
| 2010/0010493 A1 | 1/2010 | Dower |
| 2010/0023066 A1 | 1/2010 | Long et al. |
| 2010/0023126 A1 | 1/2010 | Grotz |
| 2010/0057216 A1 | 3/2010 | Gannoe et al. |
| 2010/0069910 A1 | 3/2010 | Hasselman |
| 2010/0198355 A1 | 8/2010 | Kofoed et al. |
| 2010/0212138 A1 | 8/2010 | Carroll et al. |
| 2010/0241237 A1 | 9/2010 | Pappas |
| 2010/0262150 A1 | 10/2010 | Lian |
| 2010/0305572 A1 | 12/2010 | Saltzman et al. |
| 2010/0318088 A1 | 12/2010 | Warne et al. |
| 2010/0331984 A1 | 12/2010 | Barsoum et al. |
| 2011/0029090 A1 | 2/2011 | Zannis et al. |
| 2011/0035018 A1 | 2/2011 | Deffenbaugh et al. |
| 2011/0035019 A1 | 2/2011 | Goswami et al. |
| 2011/0071645 A1 | 3/2011 | Bojarski et al. |
| 2011/0106268 A1 | 5/2011 | Deffenbaugh et al. |
| 2011/0112542 A1 | 5/2011 | Gross |
| 2011/0125200 A1 | 5/2011 | Hanson et al. |
| 2011/0125275 A1 | 5/2011 | Lipman et al. |
| 2011/0125284 A1 | 5/2011 | Gabbrielli et al. |
| 2011/0152868 A1 | 6/2011 | Kourtis et al. |
| 2011/0152869 A1 | 6/2011 | Ek et al. |
| 2011/0166608 A1 | 7/2011 | Duggal et al. |
| 2011/0190829 A1 | 8/2011 | Duggal et al. |
| 2011/0218542 A1 | 9/2011 | Lian |
| 2011/0245835 A1 | 10/2011 | Dodd et al. |
| 2011/0253151 A1 | 10/2011 | Tochigi et al. |
| 2011/0276052 A1 | 11/2011 | Hasselman |
| 2011/0295380 A1 | 12/2011 | Long |
| 2012/0010718 A1 | 1/2012 | Still |
| 2012/0046753 A1 | 2/2012 | Cook et al. |
| 2012/0053591 A1 | 3/2012 | Haines et al. |
| 2012/0053644 A1 | 3/2012 | Landry et al. |
| 2012/0083789 A1 | 4/2012 | Blakemore et al. |
| 2012/0109131 A1 | 5/2012 | Vasarhelyi et al. |
| 2012/0109326 A1 | 5/2012 | Perler |
| 2012/0130376 A1 | 5/2012 | Loring et al. |
| 2012/0136443 A1 | 5/2012 | Wenzel |
| 2012/0185057 A1 | 7/2012 | Abidi et al. |
| 2012/0191210 A1 | 7/2012 | Ratron et al. |
| 2012/0239045 A1 | 9/2012 | Li |
| 2012/0245701 A1 | 9/2012 | Zak et al. |
| 2012/0271314 A1 | 10/2012 | Stemniski et al. |
| 2012/0271430 A1 | 10/2012 | Arnett et al. |
| 2012/0277745 A1 | 11/2012 | Lizee |
| 2013/0041473 A1 | 2/2013 | Rouyer et al. |
| 2013/0116797 A1 | 5/2013 | Coulange et al. |
| 2014/0020690 A1 | 1/2014 | Triplett |
| 2014/0236157 A1 | 8/2014 | Tochigi et al. |
| 2014/0276853 A1 | 9/2014 | Long et al. |
| 2014/0296995 A1 | 10/2014 | Reiley et al. |
| 2014/0309640 A1 | 10/2014 | Smith et al. |
| 2014/0336658 A1 | 11/2014 | Luna et al. |
| 2015/0045801 A1 | 2/2015 | Axelson et al. |
| 2016/0135815 A1 | 5/2016 | Loring et al. |
| 2016/0135857 A1 | 5/2016 | Marrero, Sr. |
| 2016/0361071 A1 | 12/2016 | Mahfouz |
| 2018/0084985 A1* | 3/2018 | Saw .................. A61B 17/1615 |
| 2018/0177511 A1 | 6/2018 | Luna et al. |
| 2018/0263639 A1 | 9/2018 | McGinley et al. |
| 2019/0059917 A1 | 2/2019 | Saltzman |
| 2019/0059918 A1 | 2/2019 | Saltzman et al. |
| 2019/0133612 A1 | 5/2019 | McGinley |

(56) References Cited

U.S. PATENT DOCUMENTS

2020/0281727 A1* 9/2020 Dang .............. A61B 17/68
2021/0298770 A1* 9/2021 Allard .............. A61B 17/15

FOREIGN PATENT DOCUMENTS

| | | |
|---|---|---|
| EP | 2967697 | 4/2018 |
| EP | 3354233 | 10/2019 |
| GB | 2480846 | 12/2011 |
| JP | H11-500035 | 1/1999 |
| JP | 2006150055 | 6/2006 |
| JP | 2007508123 | 4/2007 |
| JP | 2007518453 | 7/2007 |
| JP | 2007519477 | 7/2007 |
| JP | 2007536011 | 12/2007 |
| JP | 2009148597 | 7/2009 |
| JP | 2011526189 | 10/2011 |
| JP | 2012518517 | 8/2012 |
| JP | 2013500810 | 1/2013 |
| JP | 2013511358 | 4/2013 |
| JP | 5412334 | 2/2014 |
| JP | 2014131738 | 7/2014 |
| WO | WO 9625106 | 8/1996 |
| WO | WO 0166021 A1 | 9/2001 |
| WO | WO 2005011523 A2 | 2/2005 |
| WO | WO 2005037135 | 4/2005 |
| WO | WO 2006022923 | 3/2006 |
| WO | WO 2006023824 | 3/2006 |
| WO | WO 2006099270 | 9/2006 |
| WO | WO 2007084846 | 7/2007 |
| WO | WO 2009143374 | 11/2009 |
| WO | WO 2009158522 | 12/2009 |
| WO | WO 2010099142 | 9/2010 |
| WO | WO 2010135156 | 11/2010 |
| WO | WO 2011015863 | 2/2011 |
| WO | WO 2011063281 | 5/2011 |
| WO | WO 2011151657 | 12/2011 |
| WO | WO 2012088036 | 6/2012 |
| WO | WO 2012116089 | 8/2012 |
| WO | WO 2012158917 | 11/2012 |
| WO | WO 2013169475 | 11/2013 |
| WO | 2014020561 A1 | 2/2014 |
| WO | WO 2014152535 | 9/2014 |
| WO | WO 2015167581 | 11/2015 |
| WO | WO 2016005722 | 1/2016 |
| WO | WO 2016039762 | 3/2016 |

OTHER PUBLICATIONS

Search report issued for European patent application No. 13198280 dated Feb. 5, 2014.
International Search Report for International patent application No. PCT/US2014/027448 dated Jul. 7, 2014.
International Preliminary Report on Patentability issued for International patent application No. PCT/US2014/027448, Sep. 15, 2015, 8 pages.
Partial European Search Report issued in connection with European patent application No. 14768333.8, Oct. 26, 2016, 6 pages.
Patent Examination Report No. 1 issued in connection with Australian patent application No. 2015202080, Jul. 5, 2016, 4 pages.
First Office Action issued for Japanese patent application No. 2016-117842, Sep. 12, 2017, 5 pages.
First Office Action issued in connection with corresponding Japanese Patent Application No. 2020-016447, Apr. 6, 2021, 4 pages.
Office Action in corresponding Canadian Patent Application No. 2,904,652, Jun. 2, 2020, 6 pages.
First Examination Report issued in corresponding Australian Patent Application No. 2019213412, Sep. 3, 2020, 5 pages.
First Office Action in corresponding Canadian Patent Application No. 2,904,652, Jan. 28, 2020, 5 pages.
Final Office Action issued in connection with corresponding Japanese Patent Application No. 206-502443, May 15, 2018, 3 pages.
Extended European Search Report issued in connection with corresponding European Patent Application No. 18160378.8, Jun. 29, 2018, 7 pages.
Second Office Action issued in connection with corresponding Chinese Patent Application No. 2018071101785100, dated Jul. 16, 2016, 6 pages.
First Office Action in corresponding Japanese Patent Application No. 2018-178853, Sep. 3, 2018, 3 pages.
Examination Report No. 1 issued in connection with corresponding Australian Patent Application No. 20182000073, Dec. 24, 2018, 3 pages.
First Office Action issued in connection with corresponding Japanese Patent Application No. 2018-092289, Mar. 5, 2019, 2 pages.
Extended European Search Report and Opinion in connection with European Patent Application No. 14768333.8, dated Jan. 30, 2017, 10 pages.
First Office Action issued in connection with Chinese Patent Application No. 2017800899442 dated Apr. 6, 2022, 8 pages.
International Search Report and Written Opinion issued in connection with International Patent Application No. PCT/US2021/025873, Sep. 2, 2021.
Orthopedic Designs North America, Inc., http://odi-na.com/?service=talon-distalfix-fermoral-nail-system, accessed via Internet, Jul. 22, 2022.
Arthrex, "Arthrex—Intramedullary Nails," https://www.arthrex.com/foot-ankle/intramedullary-nails, accessed via Internet, Jul. 22, 2022.
Inbone II Total Ankle Surgical Technique, Wright Medical Technology, Inc., Mar. 12, 2014, 64 pages.
Infinity Total Ankle System Surgical Technique, Wright Medical Techology, Inc., Aug. 8, 2015, 76 pages.
First Examination Report issued in connection with Australian Patent Application No. 2020277219, Nov. 19, 2021, 7 pages.
International Search Report and Written Opinion issued in connection with International Patent Application No. PCT/US2016/023729, Feb. 14, 2017, 14 pages.
First Examination Report issued in connection with Australian Patent Application No. 2019246766, Apr. 17, 2020, 9 pages.
Supplementary European Search Report issued in connection with corresponding European Patent Application 16895669.6 Oct. 21, 2019, 6 pages.
Office Action in connection with corresponding Canadian Patent Application No. 3,014,284, Jun. 17, 2019, 4 pages.
First Examination issued in connection with Australian Patent Application No. 2016398429, Jan. 21, 2019, 4 pages.

* cited by examiner

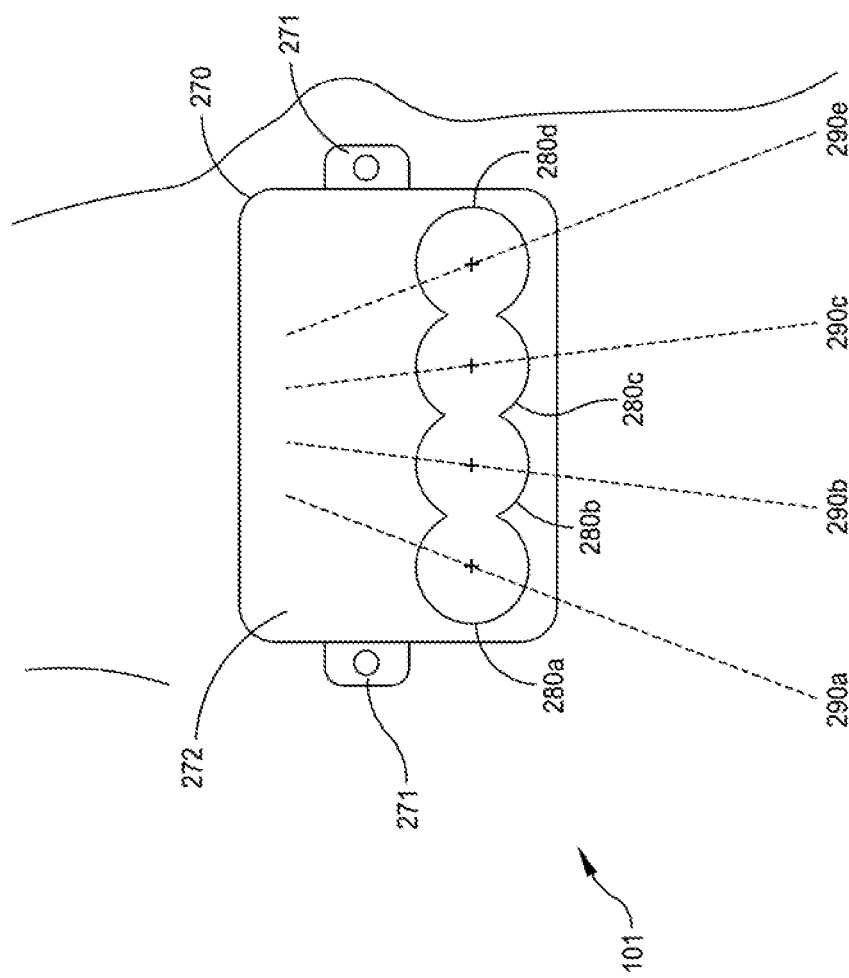

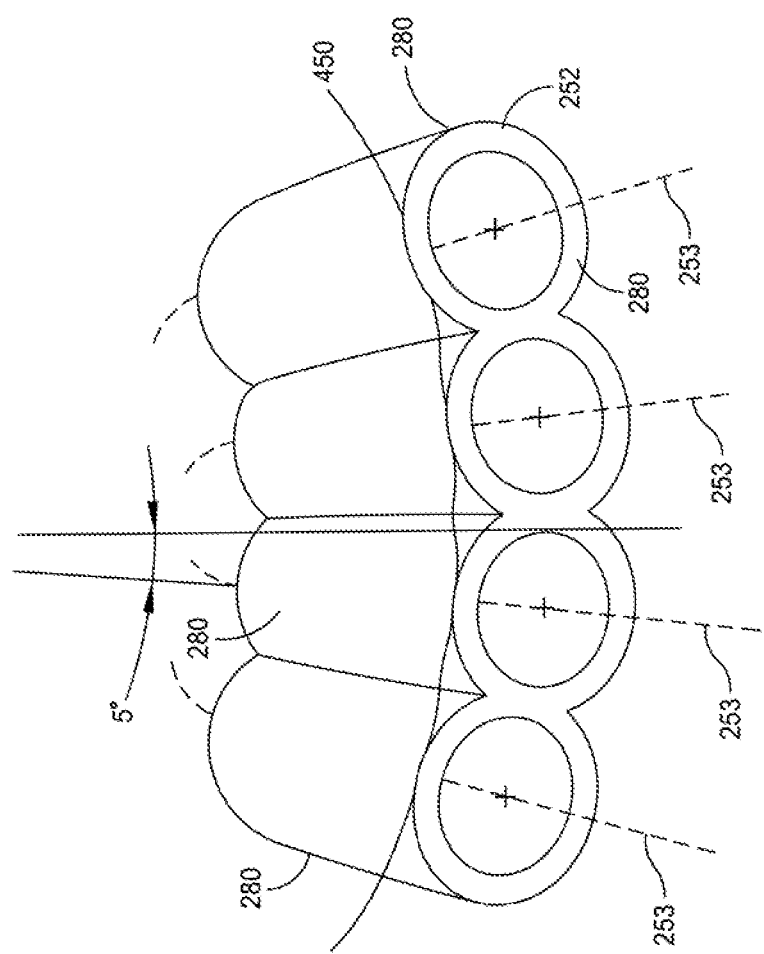

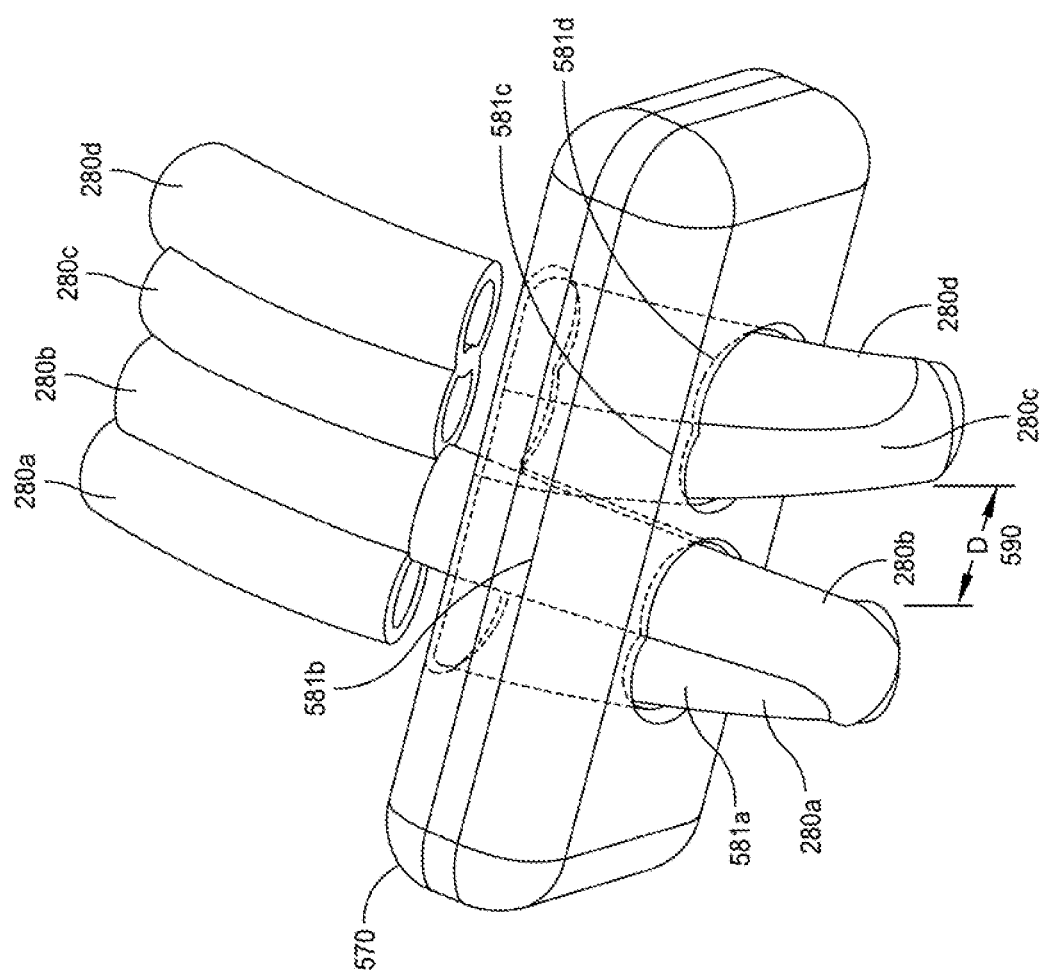

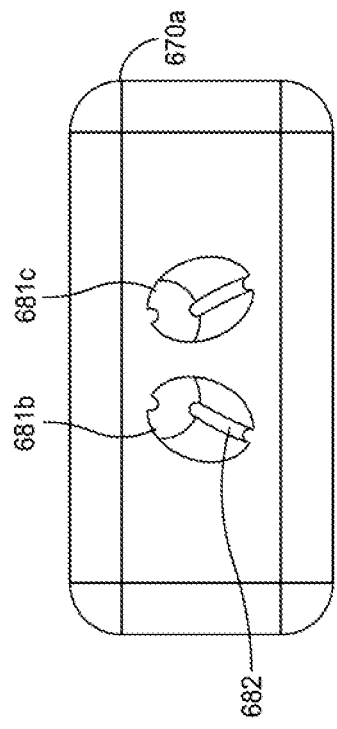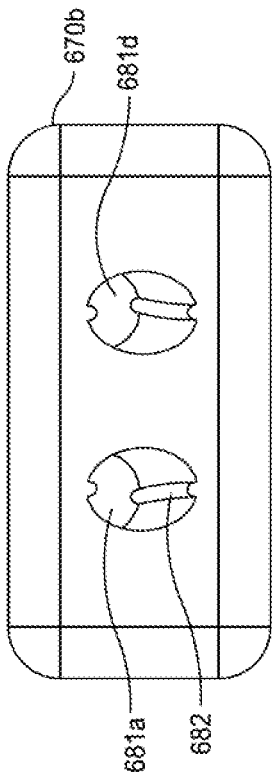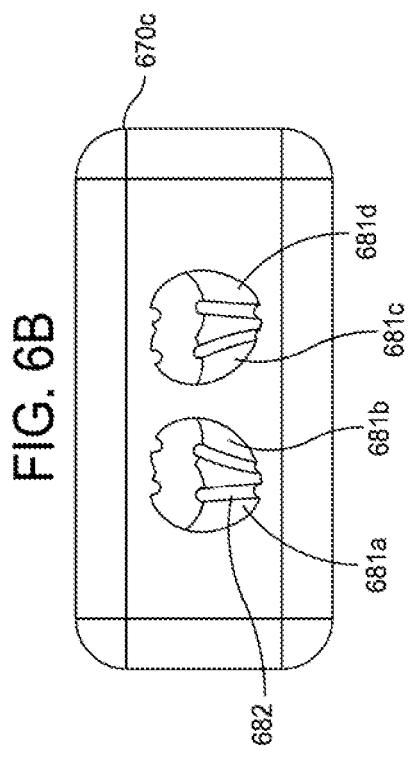

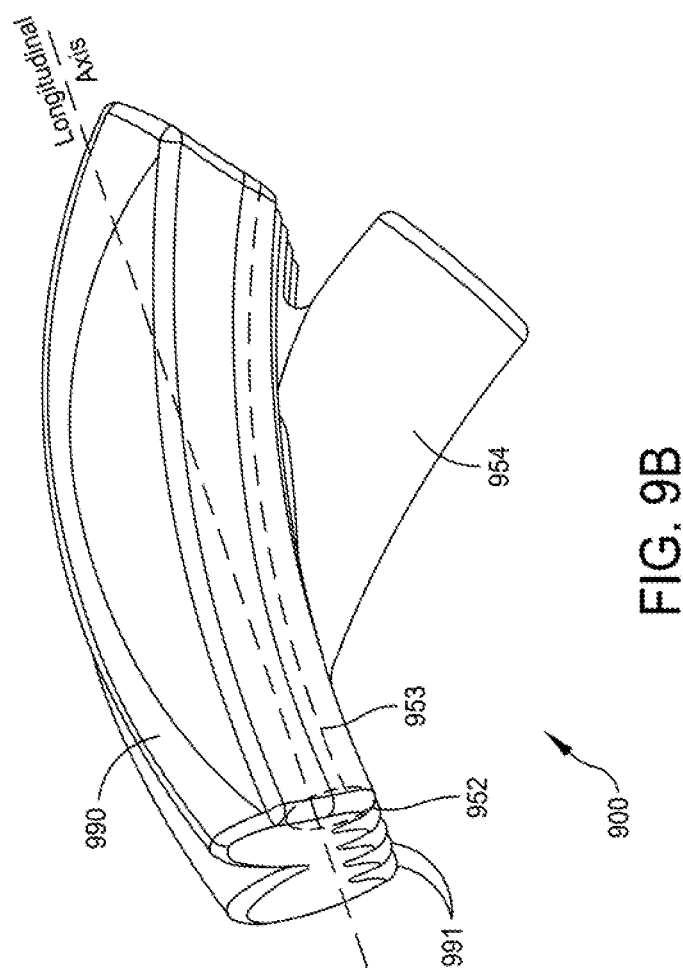

METHODS AND APPARATUS FOR JOINT REPAIR

RELATED APPLICATIONS

This application is a non-provisional of and claims priority benefit of co-pending provisional application 63/267,240 entitled "METHODS AND APPARATUS FOR JOINT REPAIR" filed Jan. 28, 2022, the entirety of which is herein incorporated by reference.

TECHNICAL FIELD

The disclosed subject matter relates generally to a system and method for preparing a bone surface to accept a joint insert while minimizing bone material removal and creating a secure seat for the joint insert. The disclosed subject matter bores (reams, machines, drills) a plurality of laterally arranged concave channels (troughs) in the joint end of the bone, using an arced drill drive and a drill guide with a plurality of arced guide bores and provides the joint insert with cooperating convex ridges, such that the joint insert will positively seat with minimal need of pins, pegs or screws to provide stability.

BACKGROUND

Removing minimal amounts of talar and tibial bone is especially challenging in osteopenia patients. Thus there is a need for more precise preparation with a minimal depth of bone removal. Current anterior TAR techniques take a large amount of bone from a flat cut in a concave surface. Other require a lateral approach which has other disadvantages. The anterior and lateral approaches have pros and cons regarding their respective soft tissue complications, osteotomy necessity, orientation of the bone cut and gutter visualization. FIG. 1 illustrates a prior art technique showing the tibia 102, talus 103 and the fibula 105. As shown through the progression in FIG. 1, the tibia 102, and talus 103 are both shaped to have flat surfaces 112 and 113 respectively, because of the concave shaft of the joint end of the tibia 102, a significant amount of heathy bone is removed. An improved anterior TAR technique and instruments are needed.

One prior art method for drilling channels in bone, described in Patent Publication US 2005/0267481, includes attaching a drill assembly to the frame assembly, so a drill bit of the drill assembly will follow predetermined circular path in fixed relation with the frame and moving the drill bit through the predetermined path while the drill bit is rotating to cut the channel via a pivot arm. The prior art method secures the drill assembly including the drill bit to the pivot arm assembly and rotates the drill bit using the pivot arm assembly so the drill bit traverses the predetermined path. However, the apparatus is complicated, not user friendly, limited to a single predetermined path, requiring reconfiguration/relocation of the frame for each desired channel, is incapable of following helical paths and is directed to joining bones.

SUMMARY

The embodiments described herein are directed to a system and method for bone surface preparation in joint repair. In addition to or instead of the advantages presented herein, persons of ordinary skill in the art would recognize and appreciate other advantages as well.

In some embodiments, a system for repairing a joint is presented. The system includes a joint insert; a drill guide; and, a drill assembly. The joint insert including a scalloped top surface configured to rigidly engage a prepared complimentary bone surface; a bottom surface configured to non-rigidly engage a joint surface, the bottom surface opposing the top surface. The drill guide of the presented system having a plurality of bores defined by a circular cross section and a longitudinal arc, the bores cooperate with the drill assembly to direct the sheath on a single predetermined path defined by the longitudinal arc of the respective bores. The drill assembly of the system including a rigid sheath, a flexible drive shaft within the sheath, a cutting bit at the distal end of the sheath driven via the flexible drive shaft and a driver.

The disclosed subject matter also presents a joint insert having a top surface configured to engage a prepared bone surface proximate to a joint and a bottom surface configured to non-rigidly engage a joint surface, the bottom surface opposing the top surface. The joint insert including a longitudinal axis extending from the front to the rear of the insert and a lateral axis perpendicular to the longitudinal axis; the top surface having a plurality of convex ridges, each convex ridge having an outer surface intersecting the outer surface of laterally adjacent ridges, the outer surface of each ridge defined by a constant radius longitudinal arc and a circular cross section perpendicular to and along the arc. The ridges of the joint insert configured to engage corresponding concave troughs in a prepared bone surface. In another embodiment, the ridges may be smoothed down with a secondary step involving an end shrouded side cutting arced reamer tool to accommodate non-ridged implants, along with a corresponding guide for ridge take-down. The ridges may be retained, reduced, or removed depending on surgeon preference and implant to bone interfacing.

In some embodiments, a drill guide for preparing a bone surface proximate to a joint is presented. The drill guide including a plate with front and opposing rear faces and a plurality of bores through the plate. Each of the plurality of bores are defined by a longitudinal arc and a circular cross section perpendicular to and along the arc and are configured to cooperate with a sheath of a drill assembly having substantially the same respective circular cross section and longitudinal arc, and direct the sheath on a single predetermined path defined by the longitudinal arc of the respective bores.

In yet other embodiments, a method for repairing a joint between two bones is presented. The method includes exposing the joint; boring a plurality of adjacent troughs in the proximal or distal end of one of the bones to form a scalloped surface; and, seating a joint insert with a cooperating surface on one side on the joint insert on the prepared scalloped surface.

BRIEF DESCRIPTION OF THE DRAWINGS

The features and advantages of the present disclosures will be more fully disclosed in, or rendered obvious by the following detailed descriptions of example embodiments. The detailed descriptions of the example embodiments are to be considered together with the accompanying drawings wherein like numbers refer to like parts and further wherein:

FIG. 3 illustrates the drill guide positioned on the ankle in accordance with embodiments of the disclosed subject matter;

FIG. 4 illustrates an example of a plurality of bores which define the scalloped surface of the bone forming a saddle according to an embodiment of the disclosed subject matter;

FIGS. 5A and 5B illustrate the bore defined by the drill guide and the resultant scalloped surface in accordance with embodiments of the disclosed subject;

FIGS. 6A-6C illustrate drill guides with keyed guide bores according to embodiments of the disclosed subject matter;

FIGS. 9A-9D illustrate various views of a joint insert cooperating with the scalloped bone surface according to embodiments of the disclosed subject matter;

DETAILED DESCRIPTION

Figure 1:
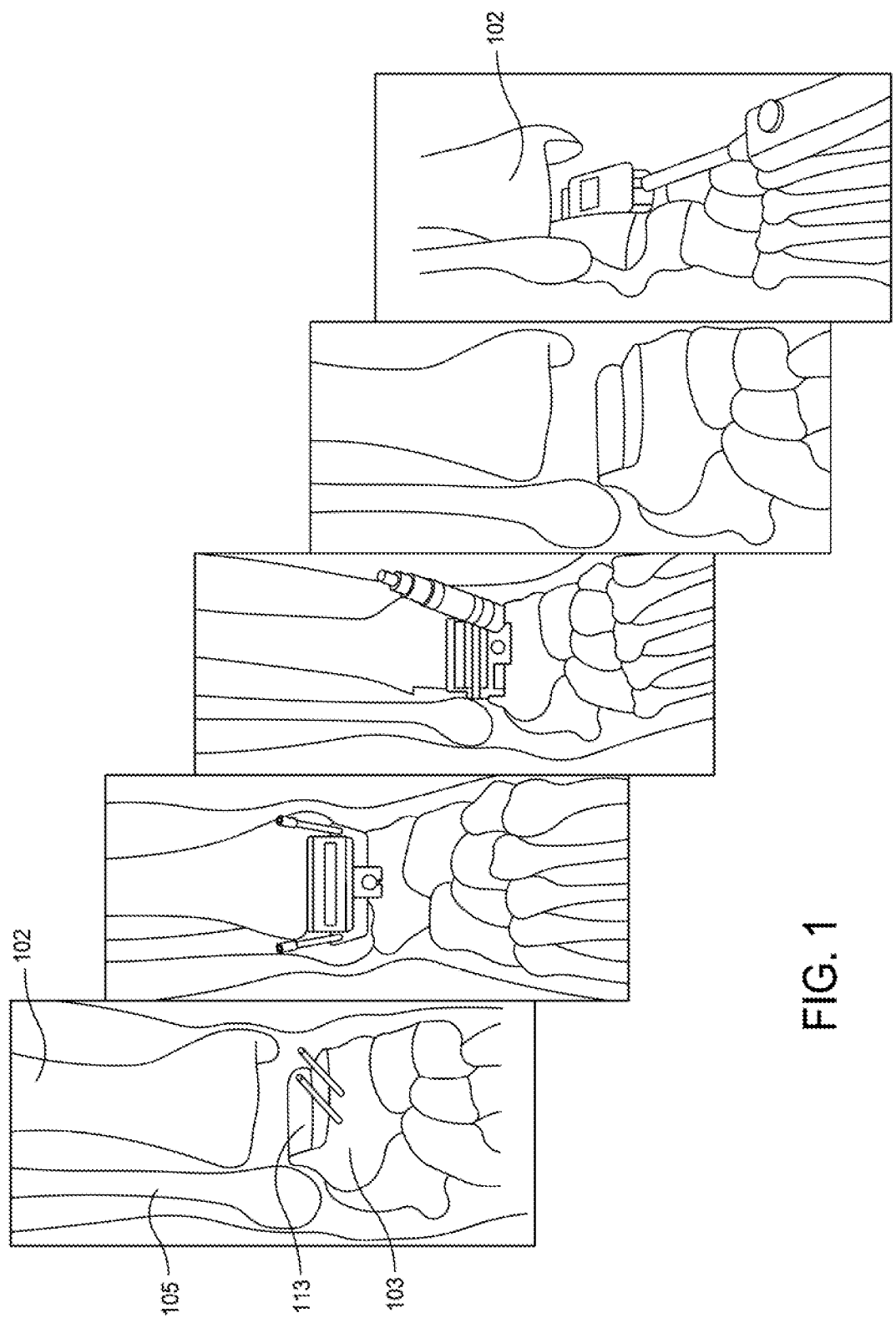
FIG. 1 is an illustration of a prior art method for preparing a bone surface in the ankle.

The description of the preferred embodiments is intended to be read in connection with the accompanying drawings, which are to be considered part of the entire written description of these disclosures. While the present disclosure is susceptible to various modifications and alternative forms, specific embodiments are shown by way of example in the drawings and will be described in detail herein. The objectives and advantages of the claimed subject matter will become more apparent from the following detailed description of these exemplary embodiments in connection with the accompanying drawings.

It should be understood, however, that the present disclosure is not intended to be limited to the particular forms disclosed. Rather, the present disclosure covers all modifications, equivalents, and alternatives that fall within the spirit and scope of these exemplary embodiments. The terms "couple," "coupled," "operatively coupled," "operatively connected," and the like should be broadly understood to refer to connecting devices or components together either mechanically, electrically, wired, wirelessly, or otherwise, such that the connection allows the pertinent devices or components to operate (e.g., communicate) with each other as intended by virtue of that relationship.

Figure 2A:
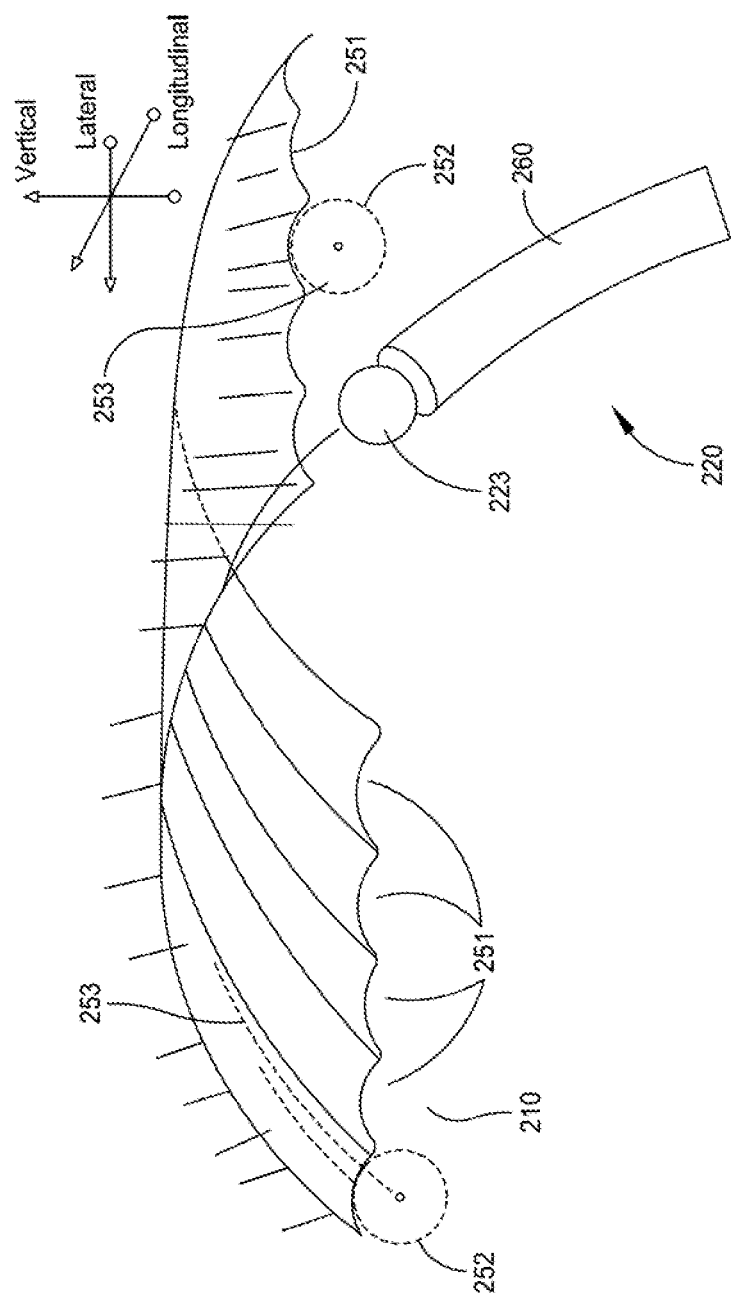
FIG. 2A is an illustration of a scalloped bone surface associated with embodiment of the disclosed subject matter.
Figure 2B:
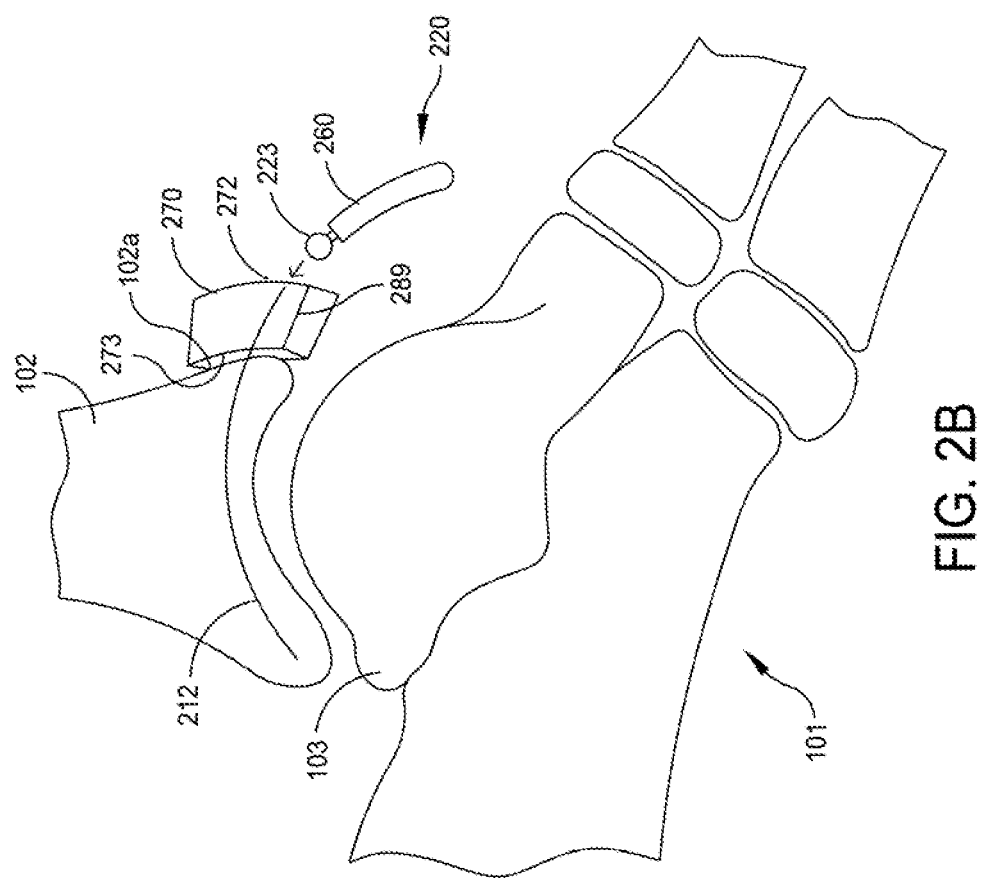
FIG. 2B is an illustration of the boring of troughs in the tibia with a drill assembly to create the scalloped bone surface illustrated in FIG. 2A in accordance with embodiments of the disclosed subject matter.

FIG. 2A illustrates an example of a scalloped bone surface 210 of and/or created by embodiments of the disclosed subject matter, the scalloped bone surface 210 includes a plurality of adjacent troughs 251 which are defined by an arc 253 extending generally in the longitudinal direction and a circular cross section 252 in the lateral direction (perpendicular to the arc) along the arc 253 forming the defining bores 280. In forming the scalloped surface 210, the circular cross sections 252 defining each trough 251 intersect the circular cross sections 252 defining adjacent troughs 251. As shown in FIG. 2A, the longitudinal arc 253 is circular, however the arc may also be helical as described in FIG. 8. Helical arcs present additional access advantages in which drill bit 223 may better avoid the tibial anterior tendon or neurovascular bundle, yet still create the desired scalloped surface 210. FIG. 2B shows the arrangement of the drill guide 270 with respect to the tibia 102 and the talus 103 of ankle 101. The rear surface 273 of the drill guide 270 may be advantageously contoured to match the vertical surface 102a of the tibia 102. The drill assembly 220, including the bit 223 and sheath 260 are guided via guide bore(s) 281 in the drill guide 270 to remove bone in order create adjacent troughs at the end of the tibia 102 to form the prepared surface 210 (the prepared tibia surface 212 as shown). The circular cross section 252 of the bores for example when used for the tibia and/or talus may be around 6 mm in diameter.

The arched bores 280 may be reamed (bored/drilled) in parallel planes. Additionally, troughs 251 can be reamed in planes angularly offset from one another with same or different arc diameters to create the scalloped shape of the prepared bone surface 210. The drill guide and implant surfaces may correspond (cooperating) in contours for any geometry (topography) and predetermined sizes. The center of rotation for the arcs may extend inward, parallel, or outward. Additionally, the guide bores 281 of the drill guide 270 directs the drill assembly 220 in a repeatable position to ensure contours (troughs) match the joint implant contours (convex ridges). The drill guide may further include docking points, with two lateral tabs with a through hole for pinning so as to retain the relative position between bone and drill guide. This system may also lock/interface with surgical pins or frames already in place and there are many variations on the design of a drill assembly 220 to work around the anatomy while providing positive registration of the guide(s) and drill assembly 220. Registration may include orientation steps to coordinate patient anatomy with a guided instruments or computer system using reference bodies, optical, haptic, or fluoroscopic markers to orient surgical steps in 3D space with the patient anatomy. Additionally it is envisioned that arthroscopic techniques for lavage of debris and thermal regulation of the surgical site may be utilized in embodiments of the disclosed subject matter.

While not shown, both the tibia surface and talus surface may be prepared using the same drill guide 270 and drill assembly 220 by repositioning the drill guide 270 from the tibia to address the talus. Alternatively, the bores 280 may be sized such that both the tibia and talus are prepared simultaneously by the advancement of the drill bit 223 along the defined arc, cutting the scalloped surface of the tibia 212 with the top of the drill bit 223 and cutting the scalloped surface (not shown) of the talus 103 with the bottom of the drill bit 223 at the same time.

Figure 13A:
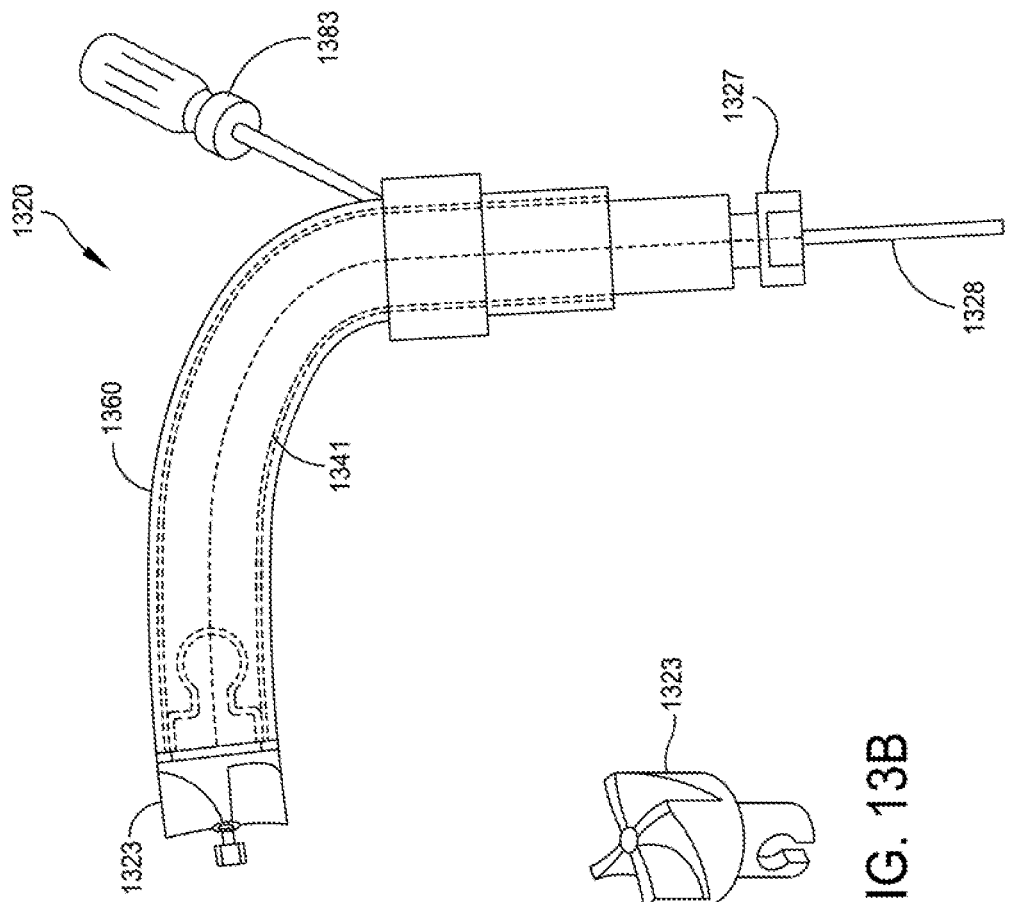
FIGS. 13A and 13B illustrate a sleeved drill assembly and bit respectively for use with embodiments of the disclosed subject matter.
Figure 13B:
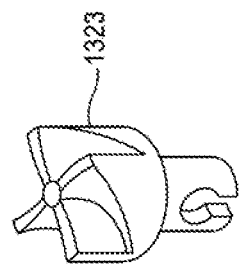

The cutting drill bit 223 may extend along the path while the drill assembly is held by hand, or a robotic controlled arm, restricted by the drill guide 270. The drive portion of drill assembly 220 need not be aligned with the predetermined path but may be introduced utilizing a 90 degree gear box to convert torque to the arc sleeve/sheath 260 of the drill assembly 220. The drill assembly 220 may utilize flexible structures known in the art (e.g. laser cut modular head IM reamer). Alternative embodiments may utilize an in-line power driver, such as U.S. Pat. No. 5,395,188 discussed below with respect to FIG. 10, along with modifications to enable its use as surgical equipment or the embodiment described with respect to FIGS. 13A and 13B. FIG. 13A shows the drilling assembly 1320 sans the driver. The drilling assembly 1320 includes a rotating bit 1323, a sheath 1350 and flexible drive shaft 1341. Additionally, an anti-torque device/handle/robot fixture 1383 may advantageously hold the drilling assembly 1320 and prevent the sheath from rotating with the bit 1323. FIG. 13B is an isometric view of the rotating bit 1323 according to some embodiments of the disclosed subject matter. A guide wire 1328 may be used for directing the bit to the entry point of the bore, the guide wire 1328 runs through the center of the driver attachment 1327, sheath 1360, drive shaft 1341, and through the center of the bit 1223.

Figure 10:
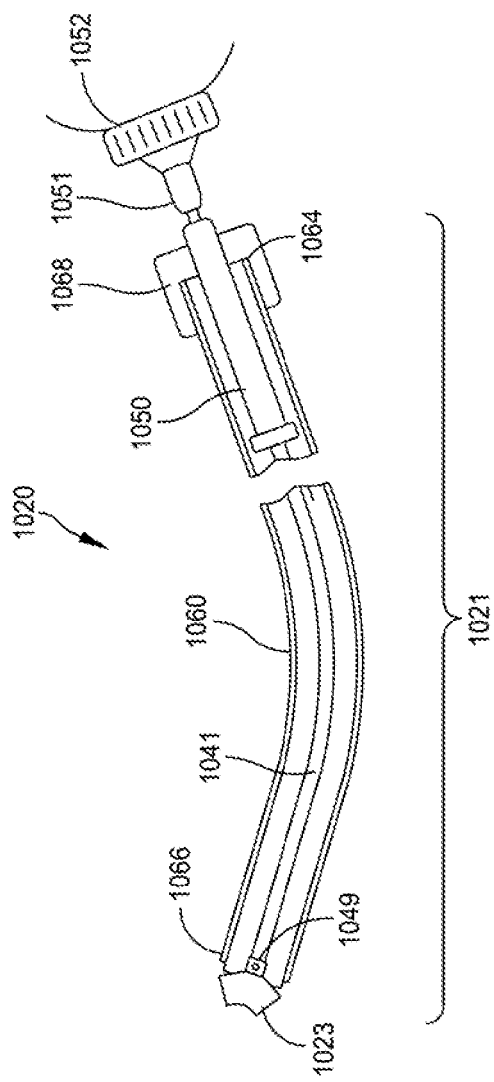
FIG. 10 illustrates a prior art sleeved drill assembly.

An example of a drill assembly is described in U.S. Pat. No. 5,395,188, the entirety of which is hereby incorporated by reference. Turning to FIG. 10, for guiding the drill bit 1021 along the curved path to drill a hole in a desired direction, the drill assembly 1020 includes a curved guide sleeve or tube 1060 between an inlet end 1064 and terminating in an outlet end 1066. For supporting the drill bit 1021 in the guide tube 1060, a cap bushing 1068 is threaded securely to the inlet end 1064 of the guide tube 1060. The bushing journals the drill shaft 1050 for rotating and sliding movement through the curved tube thereby enabling the drill bit 1021 to project outwardly through the outlet end 1066 of the tube 1060 into an adjacent surface through which a hole is to be drilled. The flexible shaft 1041 of the drill bit assembly 1021 is a stiffly-flexible coiled wire cable, the coils of which are tightly wound to produce a strong flexible shaft. The cutting bit 1023 is secured to one end of the cable 1041 by a sleeve connector 1049 crimped and secured to the cutting bit 1023 and receiving an inserted end of the cable. For engagement with a power drill tool 1052, the opposite end of the flexible cable 1041 is inserted in a stainless steel sleeve 1050 and secured thereto by a bushing or collar 1051.

With the use of the drill guide 270, the drill bit 223 of the drill assembly 220 follows a predetermined path, more particular a predetermined circular path, or predetermined helical path, in fixed relation with respect to the drill guide 270 while moving the drill bit 223 through the predetermined path while the drill bit 223 is rotating, so as to cut the channel/trough 251. The nature of the guide bores 281 within the guide 270 each correspond to one particular circular or helical path (including position and orientation of the path), such that the drill assembly (i.e., sleeve/sheath 260 and bit 223) cooperates with the guide 270 to follow substantially the path defined by the guide bore 281.

Alternatively, rather than a drilling/boring assembly that utilizes a traditional bit (i.e. rotating cutting head), the channels/troughs 251 may be formed using an ultrasonic or laser cutting heads. An ultrasonic head uses ultrasonic waves to fragment, emulsify and aspirate soft tissue and bone. One example of the use of an ultrasonic head is Stryker's Sonopet® ultrasonic Aspirator. The use of a laser head for the ablation of bone tissue allows higher accuracy and increases bone healing compared to conventional mechanical bone cutting. Both these boring heads also allow for boring channels/troughs have non-circular cross sections, as they do not rely on a rotating bit. For example, elliptical, parabolic, V-shaped, U-shaped or even irregular troughs may be bored with these alternative heads. Additionally, with precision guidance tapered troughs may be implemented with the use of these heads.

Figure 14A:
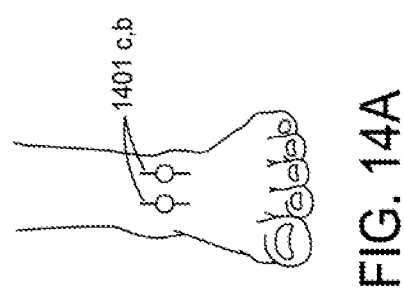
FIGS. 14A and 14B illustrate anterior entry ports for the reamer according to embodiments of the disclosed subject matter.
Figure 14B:
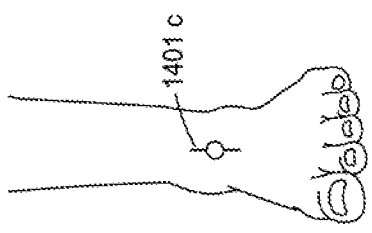

FIG. 3 illustrates a front view of the drill guide 270 on the ankle 101. The front face 272 of the drill guide 270 has a plurality of guide bores 281*a-d* that are configured to guide the drill assembly 220. While a plurality of guide bores are shown, single guide bores allowing a plurality of reaming sweeps are likewise envisioned. FIGS. 14A and 14B illustrate multiple entry portals 1401*a* and 1401*b* and a single portals 1401*c* respectively each resulting in multiple sweeps to form the prepared surface of the disclosed subject matter. The entry portals typically correspond to the number of guide bores, however each portal may be expanded to received multiple sweeps. The drill guide 270 may include attachment points 271 that allow the rigid attachment of the drill guide 270 to the bone, in this case the tibia 102. Each of the guide bores 280*a-d* are defined as noted above by a circular cross section 252 along an arc 253 or helix. As shown in FIG. 3 each of the arcs 253 may lie within respective planes 290*a-d* that are not parallel to one another. The defining planes 290*a-d* in which the defining arc 253 lie may be parallel or oblique and their intersections may be located outside of the guide 270, with respect to helical arcs, such a plane is not defined.

FIG. 4 illustrates a plurality of bores 280 which define the scalloped surface 210 of the bone formed in a saddle. As shown in FIG. 4, a lateral curve 450 tangent to each of the circular cross sections 252 of the respective bores 280 has a positive curvature (meaning the center of curvature is above) and thus will form a convex surface on the bone surface, while the arcs 253 or helix defining the bores 280 have a negative curvature (meaning the center of curvature is below) and thus will form a concave surface on the bone surface. These convex curvatures in the lateral direction along with the concave curvature in the longitudinal direction will result in a saddle topography for the scalloped surface. It is also envisioned the scalloped surface 210 may be formed with a saddle in the opposite direction, such that the scalloped surface is concave in the lateral direction and convex in the longitudinal direction. Moreover, the scalloped surface 210 may be defined as semi-hemispherical in that both in the lateral and longitudinal directions, the surface curves are both positive or both negative.

Figure 5A:
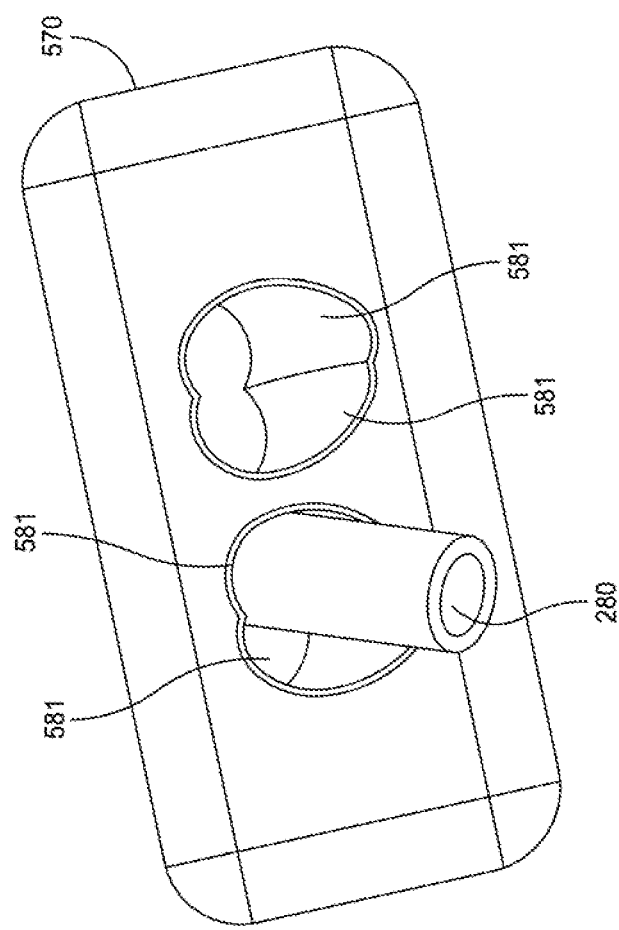

In FIG. 5A, the drill guide 570 is shown with four guide bores 581*a-d*, the first set 581*a*, 581*b* intersecting within the guide 570 and the second set 581*c*, 581*d* also intersecting within the drill guide 570. The orientation of the guide bores 581 within drill guide 570 allow for off center access to create the scalloped surface. As noted earlier, this access advantageously avoids the tibialis anterior tendon and/or neurovascular bundle. FIG. 5B further illustrates this access in which the adjacent bores 280 overlap to create the desired scalloped surface, yet the bores 280 are separated laterally a distance D 590 as they approach the drill guide 570. This approach for example may allow a 10 degree medial entry, as well as lateral entry. Entry into the joint space may include arthroscopic techniques known in the surgical arts. In one embodiment, the arched reamers may pass through a single portal to create an array of contoured sweeps to remove bone. In another embodiment, there may be multiple portals which allow for sweeps at different entry angles to form a singular prepared joint surface within the patient's anatomy. In the case of multiple incision portals, the implant may comprise multiple components which are partitioned outside of the patient and assembled within the patient to combine and operate as an implant system.

FIG. 6A shows a drill guide 670*a* with two guide bores 681*a* and 681*b*. The bores defining the guide bores 681*b,c* are inclined towards each other intersecting behind the drill guide 670*a*. The guide bores 681*b* and 681*c* also include a key 682 at the top and bottom of the guide bores 681, while two are shown for each guide bore, multiple keys, a single key or no keys are envisioned. The key 682 interacts with a respective keyway on the drill assembly 220 to precisely guide the drill assembly 220 along the predetermined arc defining the guide bores 681 and desired scalloped surface. FIG. 6B shows guide bores 681*a* and 681*d* in drill guide 670*b* these guide bores diverge from one another and thus the defining arcs intersect in front of the drill guide 670*b*. Guide bores 681*a* and 681*d* also include keys 682 that interact with respective keyways on the drill assembly (not shown). Drill guides 670*a* and 670*b* may be used sequentially to prepare the scalloped surface, boring the troughs associated with guide bores 681*b* and 681*c*, then positioning drill guide 670*b* and boring the troughs associated with guide bores 681*a* and 681*d*. The same guide bores 681 may also be incorporated into one drill guide 670*c* as shown in FIG. 6C. In FIG. 6C, the set of guide bores 681*a-d* are created in drill guide 670*c*. While the guide bores overlap, the shape of the bores and the respective keys define four distinct arc paths and thus result in the same scalloped surface as if both the drill guides 670*a* and 670*b* were uses sequentially, however advantageously, the use of the combined drill guide 670*c* only requires one positioning of the drill guide, reducing time, effort and opportunities for misalignment.

Figure 7:
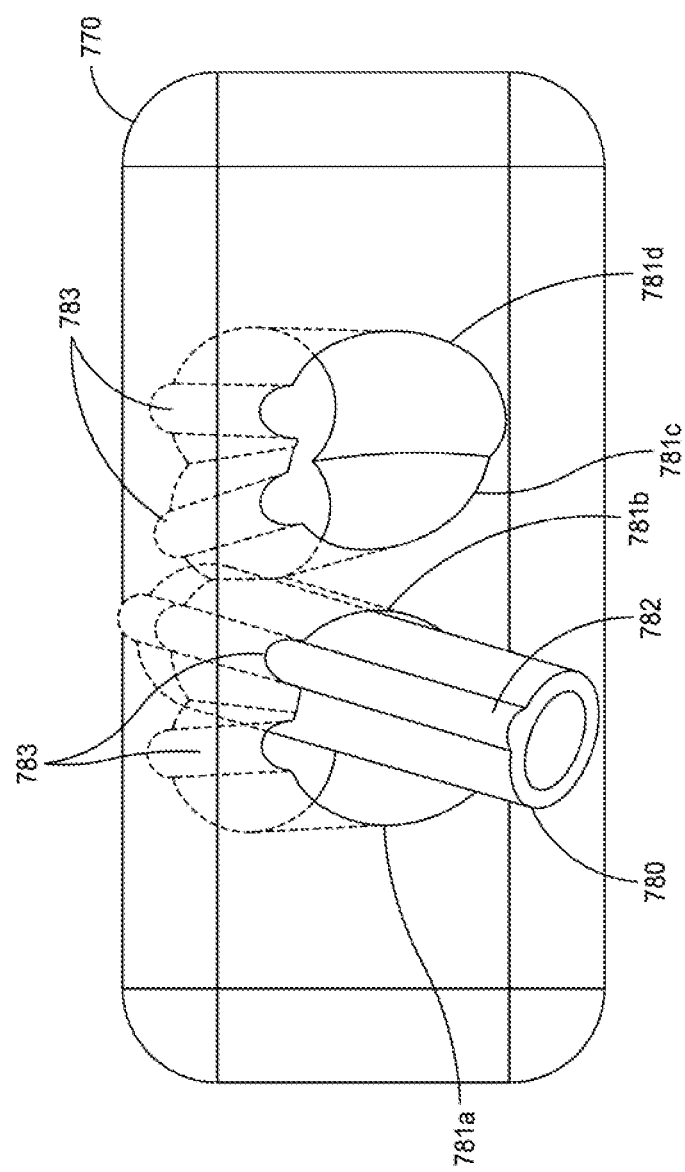
FIG. 7 illustrates a drill guide with keyways in the guide bores according to embodiments of the disclosed subject matter.

FIG. 7 illustrates a drill guide 770 in which the keyways 783 are defined within the guide bores 781*a-d* and the key 782 is on the sleeve/sheath of the drill assembly defined by bore 780. In the drill guides 770 utilizing keys or keyways, the configuration of the drill bit 223 with respect to the drill assembly sleeve 260 may require adjustments. For example in the drill guide 770 with keyways in the guide bores 781, the drill bit may be of a larger diameter than the guide bores to allow the key on the drill assembly to follow the bit along the predefined arc into the bone, resulting in the subsequently created troughs of the scalloped surface to have the same radius as the bit rather than matching the sleeve of the drill assembly. Alternatively, the key 782 on the sheath may not extend along that portion of the sheath that extends into the bone, or may be located on the opposite side of the bore than that side which creates the troughs. For example, if the bottom surface of the tibia is to be prepared the key on the sleeve would be on the bottom of the bore since only the upper portion of the bore defines the troughs 251, whereas, if the top of the talus bone is being prepared via the bore, the key on the sleeve would be positioned on the top portion of the bore as to avoid contact with the talus as the drill assembly advances into the bone. Similarly, where the key is fashioned within the guide bores as shown in FIGS. 6A-D, the drill bit 223 may need to be attached to the drill assembly from the rear of the drill guide 670, such that it would not interfere with the key 682 of the drill guide 670, it such cases in may be advantageous to further recess the rear surface of drill guide to countersink the bit so that the rear surface still matches the contour of the bone. As may be appreciated, the scalloped surfaces may be prepared with the use of a single drill guide, a single drill guide repositioned one or more times or multiple drill guides used sequentially. The drill guides may be patient specific instruments designed to match the contour of the patient bone and align implantation cuts with a pre-planned position. The guides may also be selectable from a selection of standardized guides.

Figure 8:
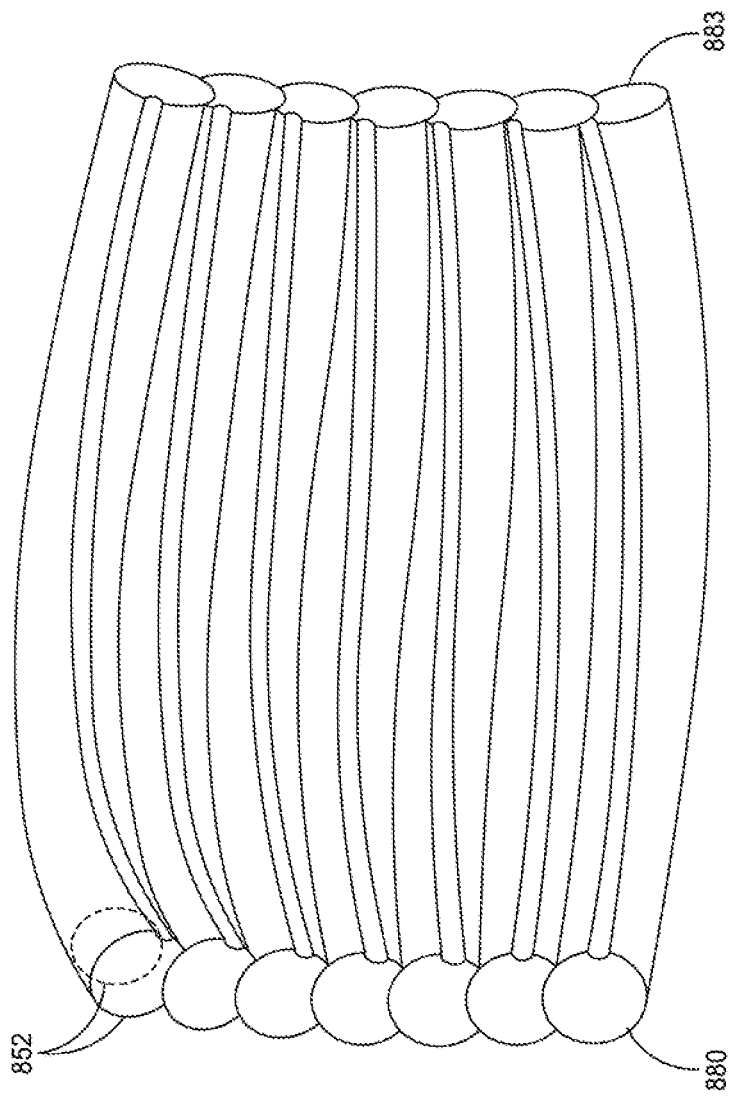
FIG. 8 illustrates helical bores defining the scalloped surface according to embodiments of the disclosed subject matter.
Figure 9A:
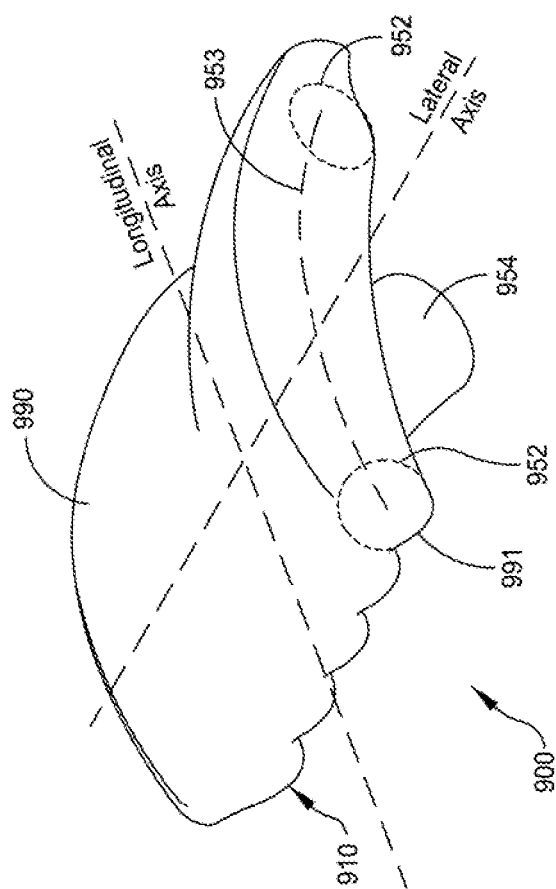
Figure 9C:
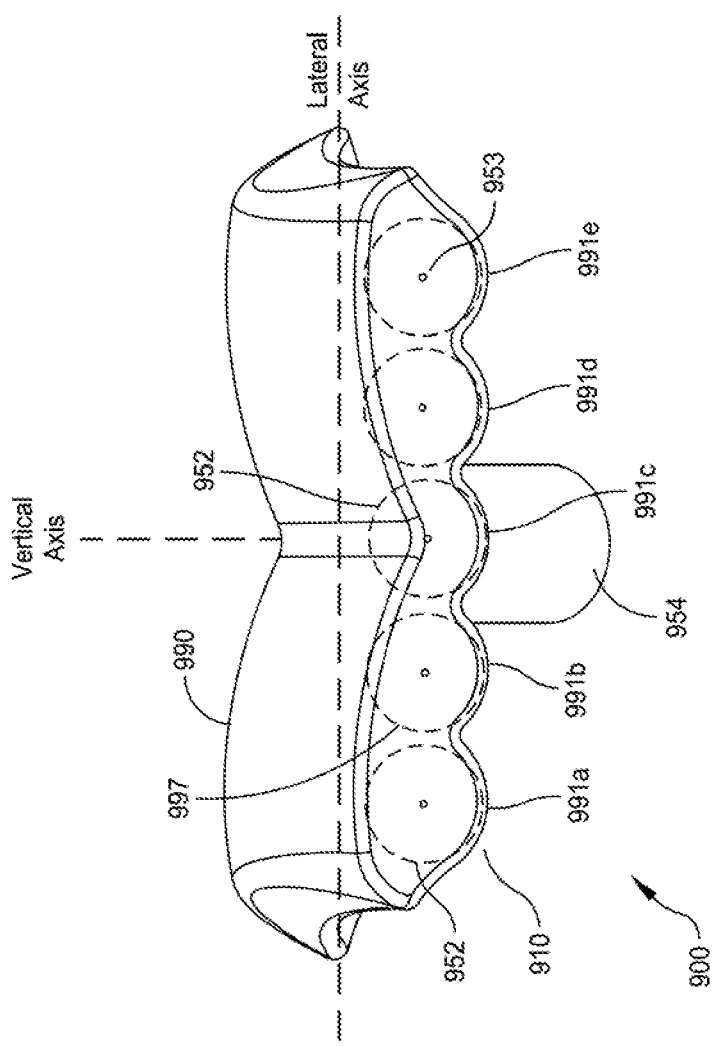
Figure 9D:
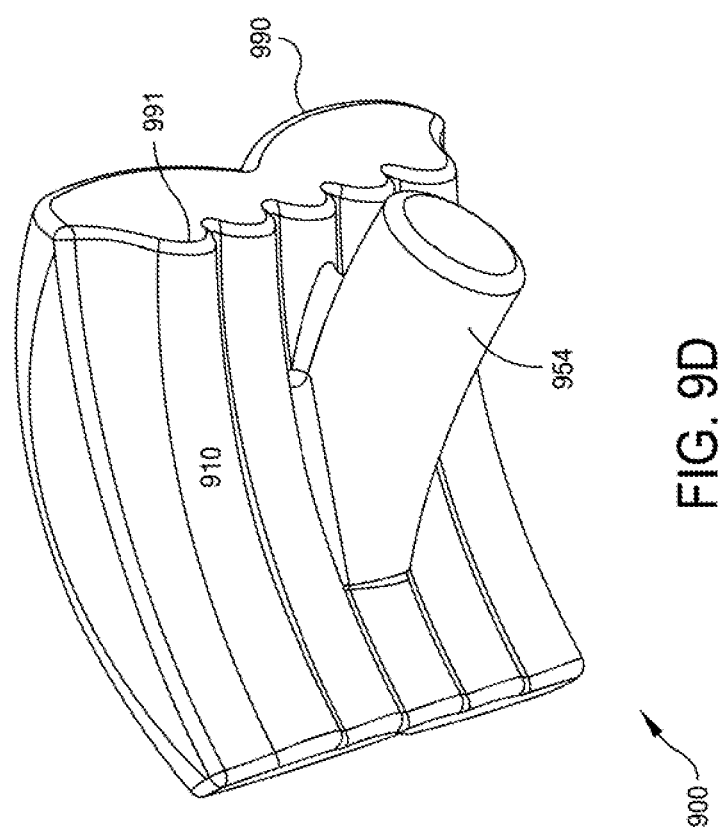

FIG. 8 illustrates the bores that define a scalloped surface in which the arcs are helical. The circular cross sections 852 are along the helical arcs. The bores 880 define both the troughs of the scalloped bone surface but also the guide bore (not shown) and the sheath of the drill assembly, in this case a keyway 883 is also shown. It should be noted that throughout the disclosure examples are presented in which each of the bores that define the guide bores, the troughs of the scalloped surface, and the ridges of the inserts have been shown with the same diameter circular cross section, however adjacent bores need not have the diameter and in some circumstances different diameter cross sections may be advantageous for several reasons including to minimize bone removal and/or stress concentrations. The arches defining the troughs and insert ridges may be in helical form as shown in FIG. 8, may be formed tight, wide, or straight (no longitudinal curvature), additionally as described elsewhere, the respective adjacent troughs may have various orientations with respect to each other, e.g. parallel, oblique, clam shell, overlapping, intersecting etc. It is envisioned that the arches may have radii ranging from 0 (a straight bore) to a 100 mm, with a bore diameter of 3-20 mm. The arches need not have a round cross section in the case of ultrasonic cutting tips or laser heads. The desired bone boring shape may utilize one tool path or a combination of straight and arched tools to achieve a net shape cavity in the patient bone.

Figure 12A:
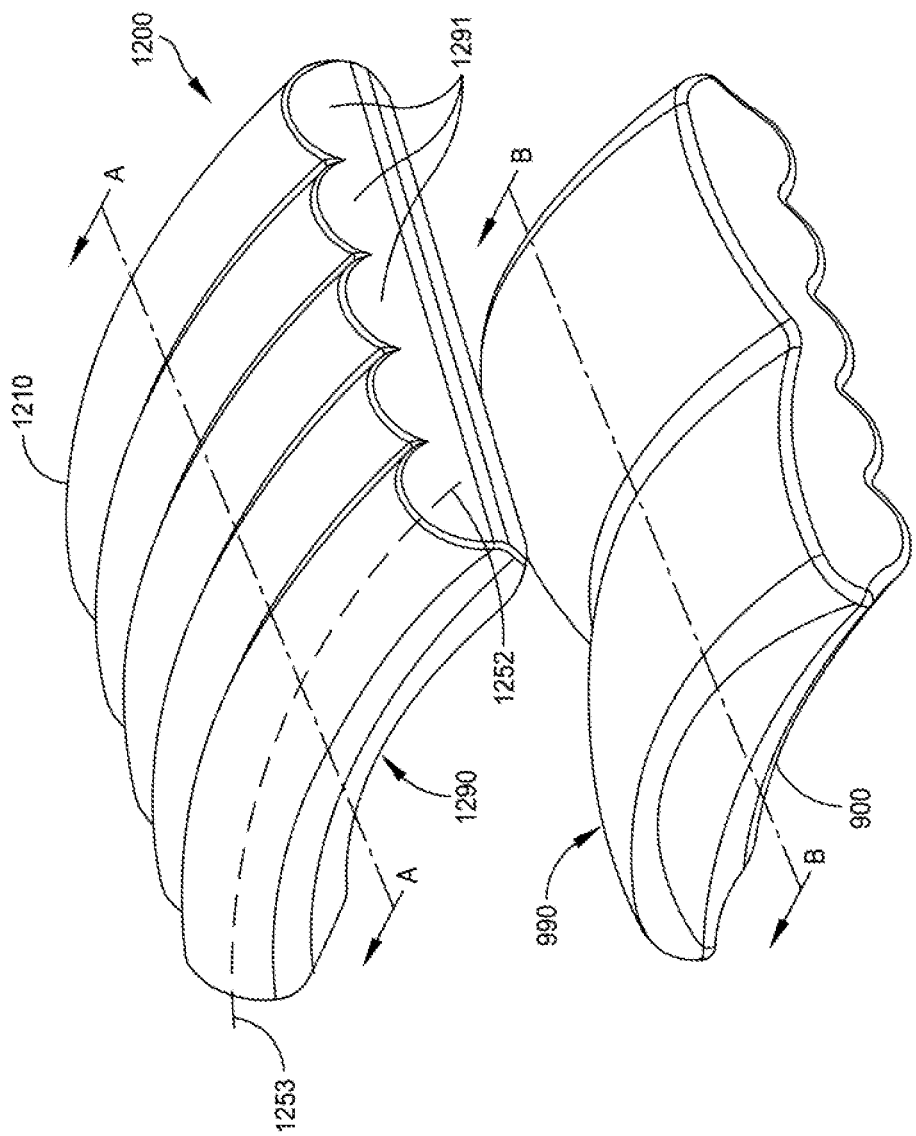
FIGS. 12A, 12B illustrate cooperating joint surfaces of an insert pair and cross sections thereof according to an embodiment of the disclosed subject matter.

An example of a joint insert (implant) 900 for engaging the prepared scalloped bone surface described above is shown in FIGS. 9A-9D. The insert 900 has a joint surface 990 proximate the joint and flexibly engages an opposing joint surface (as shown in FIG. 12A). The insert 900 has a bone engaging surface 910 that is shaped as the inverse of the scalloped bone surface discussed previously. Specifically, the bone engaging surface 910 includes a plurality of convex ridges 991, each of the convex ridges 991 defined by a circular cross section 952 along and arc 953, these convex ridges cooperate with the troughs of the scalloped bone surface defined with substantially similar circular cross sections 252 and arcs 253. Each of the convex ridges 991 extend along the longitudinal axis and are laterally adjacent to the other convex ridges 991 across the engaging surface 910. As the bone engaging surface 910 of the joint insert 900 is an inverse of its corresponding scalloped bone surface, its surface likewise may be formed with a saddle topography, be convex in both the lateral and longitudinal axis, or be concave in both the lateral and longitudinal axis. Other characteristic topographies that may be defined by the arrangement of adjacent arced bores are also envisioned.

Also shown in FIGS. 9A-9D, a peg 954 maybe received into a cooperating peg bore (not shown) in the scalloped bone surface 210 to aid in rigidly attaching the insert 900 to the bone surface. The peg 954 may be integral to the joint insert 900, or may be inserted subsequently through an aperture (not shown) in the insert 900. Additional pins, pegs and screws may also be used to rigidly attach the insert to the bone, however given the minimization of sliding paths due to the interaction of the convex ridges 991 of the insert 900 and concave troughs 251 of the scalloped bone surface 210, such additional attachment elements may not be necessary. Cavities for pegs may be formed with arched reaming drills and guides in a similar manner as the bone removal, but with inverted arch direction (see implant FIG. TBD). The joint insert 900 may be machined, molded, casts forged or 3D printed and may be constructed of ceramic, Ultra-highmolecular-weight polyethylene (UHMWPE), PEEK, metal and/or porous metal, additionally the joint insert 900 may be prepared with a coating of ceramics, Ultra-high-molecular-weight polyethylene (UHMWPE), PEEK, and/or porous metal. Implants may also be custom made for each patient (i.e. patient specific implants "PSI") with a combination of manufacturing techniques including additive sintering or 3D printing. The materials for implantation may include porous mesh as well as non-porous fabrication. The implant may include polymer spacers, bone ingrowth portions, or ceramic surfaces.

Figure 12B:
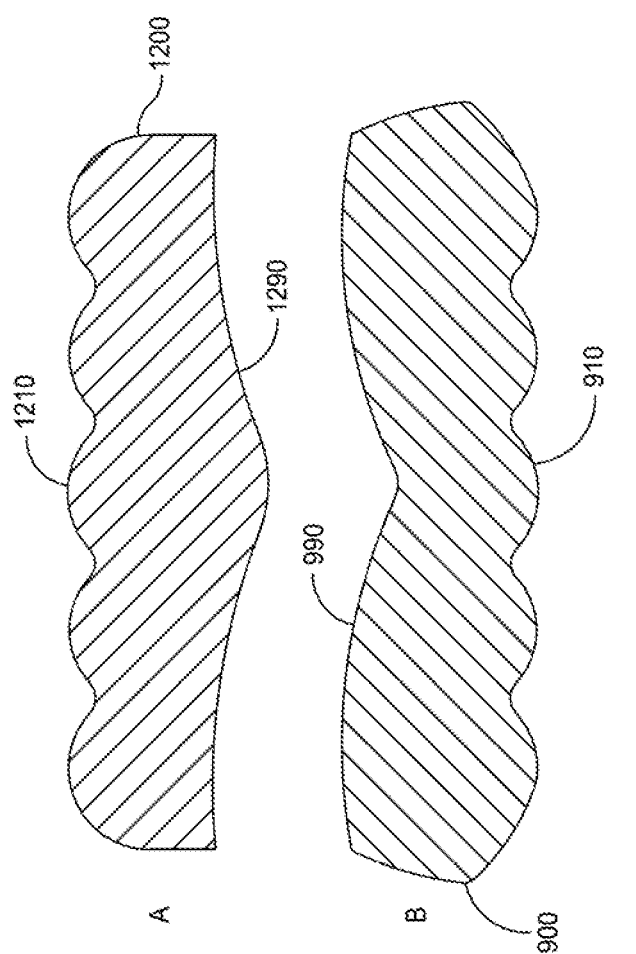
Figure 16:
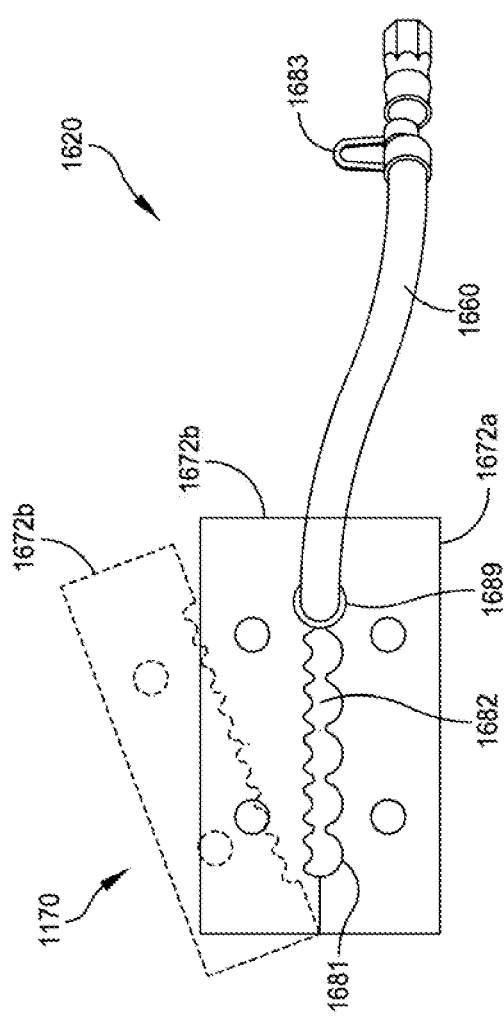

FIG. 16 illustrates a clam shell drill guide according to an embodiment of the disclosed subject matter. As shown in FIG. 16, the drilling assembly 1620 includes a sheath 1660, a counter torque device 1683 and a depth restricting device 1689 preventing the drill bit (not shown) from extending beyond the desired depth. Because of the guide notches 1682 and clearance issues, the drill bit cannot be inserted through the guide holes 1681 in the drill guide 1670. To assist, a clam shell drill guide 1670 may be used, in which the drill guide 1670 is formed of two halves shown as upper half 1672b and the lower half 1672a. In this manner one of the halves may be indexed to the patient's bone in the proper position, the sheath 1660 secured in the lower portion of the guide hole 1681, and the other half 1672b secured to the lower half 1672a, forming a complete guide hole 1681 for guiding the drilling assembly 1620. While a claim shell apparatus is shown for opening and shutting the two halves of the drill guide 1670 in FIG. 16, other mechanisms for connecting the portions is also envisioned, for example screws FIGS. 12A and 12B illustrate a mating set of joint inserts, an upper insert 1200 and the lower insert 1200b. The upper insert 1200 has a joint surface 1290 proximate the joint and flexibly engages an opposing joint surface 990 of insert 900 as described in FIGS. 9A-9D. The upper insert 1200 likewise has a bone engaging surface 1210 that is shaped as the inverse of the scalloped bone surface intended to engage, for example the tibia. Specifically, the bone engaging surface 1210 includes a plurality of concave ridges 1291 (vs convex ridges 991 for the lower insert 900), each of the concave ridges 1291 defined by a circular cross section 1252 along and arc 1253 as similarly described with respect to insert 900, these concave ridges cooperate with the troughs of the scalloped bone surface defined with substantially similar circular cross sections 252 and arcs 253. Each of the convex ridges 1291 extend along the longitudinal axis and are laterally adjacent to the other concave ridges 1291 across the engaging surface 1210. As the bone engaging surface 1210 of the upper insert 1200 is an inverse of its corresponding scalloped bone surface, the prepared bone surface likewise matching the topography of the bone engaging surface 1210. A peg as discussed with respect to insert 900 may likewise be received into a cooperating peg bore (not shown) in the scalloped bone surface 1210 to aid in rigidly attaching the upper insert 1200 to the bone surface. The peg may be integral to the upper joint insert 1200, or may be inserted subsequently through an aperture (not shown) in the insert 1200.

FIG. 12B illustrates the cooperating joint surfaces of the upper joint insert 1200 and lower joint insert 900 at the cross sections A-A and B-B respectively. As shown in FIG. 12B, the joint surface 1210 of the upper joint insert 1200 substantially matches the lower joint surface 910 of the lower joint insert 900. While not shown, in use the surfaces 1210 and 910 are in contact and transfer loads between the respective bones (e.g. tibia and talus).

Figure 11:
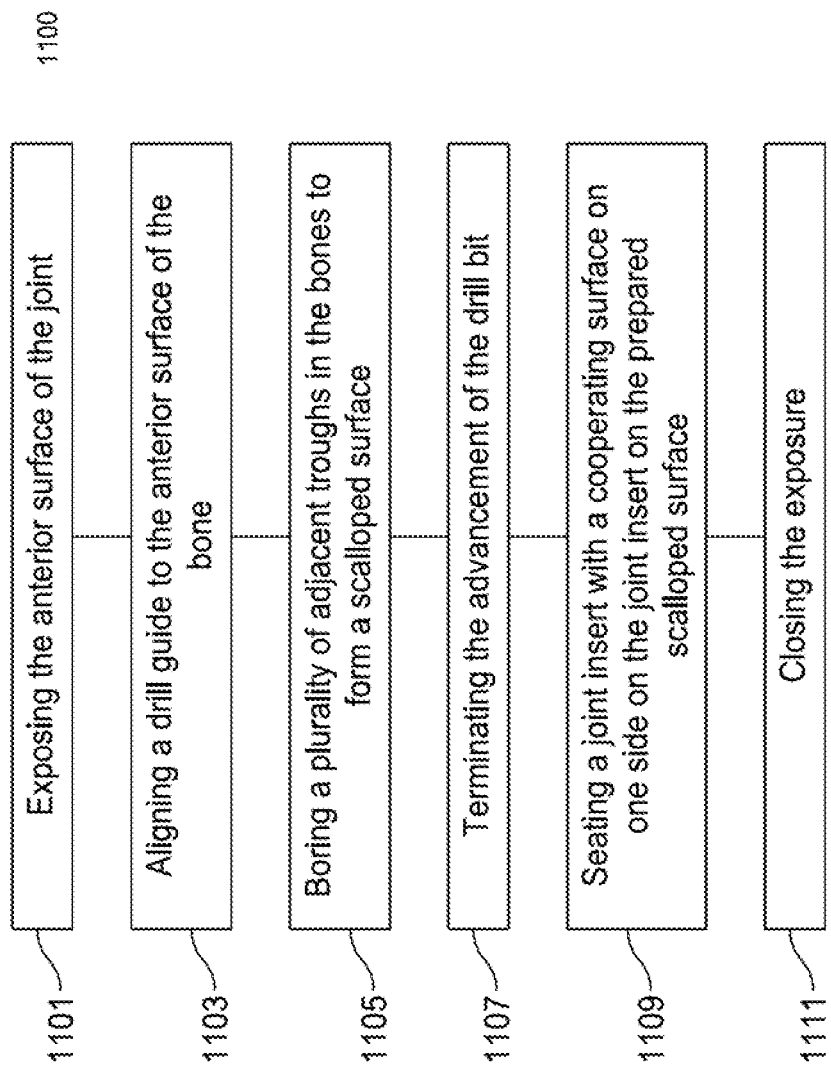
FIG. 11 illustrates a method of preparing a scalloped bone surface according to embodiments of the disclosed subject matter.

FIG. 11 shows a method 1100 for preparing a scalloped bone surface in the repair of a joint between two bones, specifically an ankle joint. As shown in Block 1101 the patient bone surface is exposed from the anterior surface. A drill guide is then aligned and affixed to the anterior surface of the bone as shown in Block 1103, alternatively the drill guide may be attached to a frame attached to the bone or if a robotic system is used in lieu of the drill guide, it may be registered with respect to the bone surface. Boring a plurality of adjacent troughs in the proximal (or distal) end of one of the bones to form a scalloped surface; by passing a bit attached to an arced sleeve and shaft along multiple pre-defined arcs into bone as shown in Block 1105, the pre-defined arcs determine by a drill guide having plural guide bores as discussed above or guided by a robotic controller. Terminating the advancement, or depth, of the drill bit to prevent the plurality of troughs from extending through the posterior rim and sides of the bone as shown in Block 1107. The termination may be accomplished with a measured depth indicator, a stop on the sleeve at a predetermined location preventing the sleeve from extending further through the drill guide, or via robotic control. In some embodiments, the troughs may extend through to the other side of the bone, however, in embodiments where the boring is terminated the unremoved bone beneficially serves to further secure and stabilize the joint insert while the bone heals to the implant 900. Thus, the depth of each bore may be advantageously pre-programed into a computer model or digital surgical plan, based on pre-op or intra-op scans. The desired cut trajectory and depth may be achieved with manual controls, patient specific guides/stops, robotic controllers, or a combination of methods. This depth control is especially useful in total ankle replacement surgery. Additionally, in these procedures plunging a cutting tool too deep, and beyond the posterior cortex of the tibia, is known to risk permanent damage to the posterior neurovascular bundle and other connective tissues. Intentionally not cutting at a depth beyond the posterior cortex will protect sensitive anatomy and stabilize the implant. The joint insert is then seated on the prepared scalloped surface as shown in Block 1109, the joint insert having a cooperating surface that is the inverse of the scalloped surface. The cooperation of the insert surface and the prepared surface stabilize the insert, restricting relative movement between the insert and scalloped surface. The wound created by the exposure is then closed using known methods as shown in Block 1111. To further stabilize the joint insert, a peg hole may also be bored into the scalloped surface and a peg integral to or separated from the insert is positioned in the peg hole. In the embodiment of hemi-arthroplasty, just one bone surface is cut while leaving the other intact. In the case of the ankle, this may include preparation of just the tibia surface while keeping the talus intact. In another embodiment, both bones on either side of the joint may be reamed simultaneously. In the case of total ankle arthroplasty the tibia and talus may be prepared with the arched reaming device.

Figure 15:
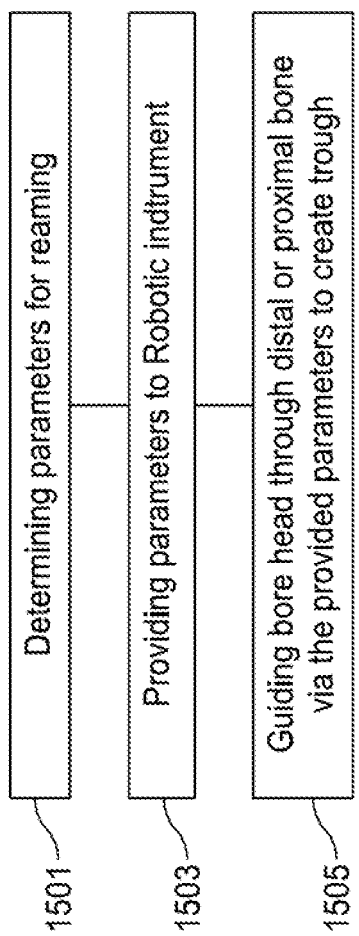
FIG. 15 is a flow chart describing the operation of boring with the use of robotic guidance according embodiments of the disclosed subject matter; and, FIG. 16 illustrates a clamshell drill guide according to an embodiment of the disclosed subject matter.

FIG. 15 illustrates an embodiment in which a robotic instrument performs the boring of the troughs in the proximal or distal end of the bone. In this embodiment the parameters of the reaming/boring are established as shown in Block 1501, the parameters may include the size and shape of the troughs, the position with respect to the joint surface, the longitudinal arc of the troughs, the respective angle of the troughs to the bone or adjacent troughs, the bone entry location, the trough terminus location, the rate of boring, and the number of troughs, etc. Once these parameters are defined, they may be provided to the robotic instrument, for example by entering manually or uploading the information as shown in Block 1503. The robotic instrument guided by the parameters may advance the boring head through the proximal or distal end of the bone to form the respective troughs in the bone as shown in Block 1505. It is also envisioned that the robot may be controlled by the surgeon in some respects, for example controlling the advancement speed of the bore head, or making adjustment to the path of the boring head. The degree of real-time control may also be limited by the parameters, or flexible such that the surgeon may engage in some free hand boring. Where surgeon real time control is used, fluoroscopic or virtual feedback would be beneficial in assisting the surgeon in controlling the robotic instrument.

Beneficial applications of the disclosed embodiments and methods are not limited to hemi-arthroplasty, but may also facilitate in addressing bi-polar, hemi, semi, and other osteochondral defects.

While the disclosed subject matter is described with respect to the ankle joint, the use of the systems, methods, guides and implants are likewise envisioned for other joints. Additionally, although the scalloped surface is described herein as being prepared with the use of a drill guide and drill assembly, other preparation techniques implementing computer control and/or robotic machining are also envisioned, with or without utilizing various components of the disclosed systems.

An aspect of the disclosed subject matter is that the general alignment of the troughs in a longitudinal manner improves the ability to position the joint insert (implant) within the joint longitudinally as the maximum thickness of the insert will generally correspond to the maximum opening on the prepared scalloped bone surface, verses lateral insertion or prior art implants, in which the minimum opening on the prepared bone surface would need to match or exceed the maximum thickness of the insert to allow insertion.

Although the methods described above are with reference to the illustrated flowcharts, it will be appreciated that many other ways of performing the acts associated with the methods can be used. For example, the order of some operations may be changed, and some of the operations described may be optional. The foregoing is provided for purposes of illustrating, explaining, and describing embodiments of these disclosures. Modifications and adaptations to these embodiments will be apparent to those skilled in the art and may be made without departing from the scope or spirit of these disclosures.

What is claimed is:

1. A method for repairing a joint between two bones comprising:
   exposing the joint;
   selecting a drill guide with a plurality of guide bores, wherein each of the plurality of guide bores are defined by a constant radius helical longitudinal arc and a circular cross section perpendicular to and along the arc;
   positioning the drill guide with respect to the joint;
   advancing a sleeve of a drill assembly through each of the plurality of guide bores;
   boring a plurality of adjacent troughs in the proximal or distal end of one of the bones to form a scalloped surface; and,
   seating a joint insert with a cooperating surface on one side on the joint insert on the prepared scalloped surface.

2. The method of claim 1, further comprising terminating the advancement of the sleeve to prevent the troughs from extending through an opposite side of the bone.

3. The method of claim 2, wherein the step of terminating the advancement comprises providing a stop on the sleeve at a predetermined location preventing the sleeve from extending further through the drill guide.

4. The method of claim 1, further comprising boring a peg hole through the scalloped surface into the bone.

5. The method of claim 1, wherein the step of boring a plurality of adjacent troughs in the proximal end of one of the bones comprises the steps of:
   defining parameters associated with the plurality of adjacent troughs;
   providing a robotic boring device with a boring head and
   advancing the boring head through each the proximal or distal end of the bone along a path defined by the parameters.

6. The method of claim 5, wherein each of the plurality of adjacent troughs have a cross section selected from the group consisting of semi-circular shape, semi-elliptical shape, V-shaped, U shaped.

7. The method of claim 5, wherein the boring head is selected from the group consisting of an ultrasonic cutting head, a mechanical bit, and a laser head.

8. The method of claim 5, further comprising terminating the advancement of the bore head to prevent the troughs from extending through an opposite side of the bone.

9. The method of claim 1, further comprising forming the joint insert, wherein the joint insert comprises:
   a top surface configured to engage the plurality of adjacent troughs a prepared bone surface proximate to a joint; the top surface having a plurality of convex ridges configure to engage the corresponding plurality of adjacent troughs in the distal or proximate end of the bone; and,
   a bottom surface configured to non-rigidly engage a joint surface, the bottom surface opposing the top surface.

10. A system for repairing a joint, comprising:
    a joint insert;
    a boring guide; and,
    a boring assembly;
    the joint insert comprising a scalloped top surface configured to rigidly engage a prepared complimentary bone surface; a bottom surface configured to non-rigidly engage a joint surface, the bottom surface opposing the top surface;
    the boring guide comprising a plurality of bores defined by a cross section and a constant radius helical longitudinal arc, the bores configured to cooperate with the boring assembly, and direct a boring head of the boring assembly on a predetermined path defined by the longitudinal arc of the respective bores.

11. The system of claim 10, wherein the boring assembly comprising a rigid sheath, a flexible drive shaft within the sheath, a bit at the distal end of the sheath driven via the flexible drive shaft.

12. The system of claim 10, wherein the bore guide comprises:
    a plate having a front face and opposing rear face and one or more bores defined through the plate between the front face and the rear face;
    each of the one or more bores defined by a longitudinal arc and a cross section perpendicular to and along the arc.

13. The system of claim 12, wherein the predetermined paths defined by the longitudinal arc of the respective one or more bores define respective planes, and the respective planes are not parallel.

14. A joint insert comprising:
- a top surface configured to engage a prepared bone surface proximate to a joint;
- a bottom surface configured to non-rigidly engage a joint surface, the bottom surface opposing the top surface;
- a longitudinal axis extending from a front of the insert to a rear of the insert and a lateral axis perpendicular to the longitudinal axis;
- the top surface having a plurality of convex ridges, each convex ridge having an outer surface intersecting the outer surface of laterally adjacent ridges, the outer surface of each ridge defined by a constant radius helical longitudinal arc and a circular cross section perpendicular to and along the helical arc;
- the plurality of ridges configured to engage a plurality corresponding concave troughs in the prepared bond surface.

15. The joint insert of claim 14, wherein the joint insert is a patient specific implant.

16. The joint insert of claim 14, wherein the joint insert is 3D printed.

17. The joint insert of claim 14, wherein the joint insert is formed of a material selected from the group consisting of: ceramic, Ultra-high-molecular-weight polyethylene (UHMWPE), PEEK, porous metal.

* * * * *